(12) United States Patent
Gotoh et al.

(10) Patent No.: US 8,173,365 B2
(45) Date of Patent: May 8, 2012

(54) METHOD FOR INHIBITING SIGNAL TRANSDUCTION, SIGNAL TRANSDUCTION INHIBITOR TO BE USED THEREIN AND USE THEREOF

(75) Inventors: Noriko Gotoh, Hino (JP); Masahiko Kuroda, Tokyo (JP); Nobuo Tsuchida, Tsukuba (JP)

(73) Assignees: The University of Tokyo (JP); Tokyo Medical University (JP); National University Corporation Tokyo Medical and Dental University (JP)

( * ) Notice: Subject to any disclaimer, the term of this patent is extended or adjusted under 35 U.S.C. 154(b) by 515 days.

(21) Appl. No.: 12/294,347

(22) PCT Filed: Mar. 23, 2007

(86) PCT No.: PCT/JP2007/056100
§ 371 (c)(1),
(2), (4) Date: Jun. 17, 2009

(87) PCT Pub. No.: WO2007/111275
PCT Pub. Date: Oct. 4, 2007

(65) Prior Publication Data
US 2010/0062978 A1    Mar. 11, 2010

Related U.S. Application Data

(60) Provisional application No. 60/785,379, filed on Mar. 24, 2006.

(51) Int. Cl.
*C12Q 1/68*     (2006.01)
*G01N 33/53*    (2006.01)
(52) U.S. Cl. ............ 435/6; 435/7.1; 435/91.2; 435/960; 435/968; 204/450
(58) Field of Classification Search .................. None
See application file for complete search history.

(56) References Cited

FOREIGN PATENT DOCUMENTS

| WO | 03/011855 A2 | 2/2003 |
| WO | 2004/072063 A1 | 8/2004 |
| WO | 2005/084691 A1 | 9/2005 |

OTHER PUBLICATIONS

Ong et al. Mol Cell Biol 2000;20:979-89.*
Sato and Gotoh, Expert Opin Ther Targets 2009;13:689-700.*
International Preliminary Report on Patentability for PCT/JP2007/056100 mailed Dec. 18, 2008.
International Search Report for International Application No. PCT/JP2007/056100 mailed Jun. 12, 2007.
Huang L. et al., "SNT-2 interacts with ERK2 and negatively regulates ERK2 signaling in response to EGF stimulation", Biochemical and Biophysical Research Communications 324 (2004) pp. 1011-1017.
Ou Rin et al., "EGF Yudo shita Saibo Transformation o Yokusei suru FRS2β/SNT-2 no Yakuwari"; Dai 64 Kai Nihon Gan Gakkai Gakujutsu Sokai Kiji, 2005, The Japanese Cancer Association Hakko, p. 374, PP2-850.
Huang L et al., "Unique role of SNT-2/FRS2β/FRS3 docking/adaptor protein for negative regulation in EGF receptor tyrosine kinase signaling pathways", Oncogene, Oct. 19, 2006, vol. 25, No. 49, p. 6457-66.
Lecia V. Sequist et al., "Molecular Predictors of Response to Epidermal Growth Factor Receptor Antagonists in Non-Small-Cell Lung Cancer", Journal of Clinical Oncology, Feb. 10, 2007, vol. 25, No. 5, pp. 587-595.
Nonko Gotoh, MD., Ph.D., "Signal transduction pathways through FRS2 docking/adaptor proteins" The 12th East Asian Joint Symposium, Nov. 20-25, 2005.
Orin et al., "FRS2β/STN-2 ni yoru EGF Juyotai Family Signal Dentatsu no Yokusei Seigyo", Dai 65 Kai Nihon Gan Gakkai Gakujutsu Sokai Kiji, 2006, The Japanese Cancer Association Hakko, pp. 39 to 40, 0-045.

\* cited by examiner

*Primary Examiner* — Q. Janice Li
(74) *Attorney, Agent, or Firm* — Cantor Colburn LLP

(57) ABSTRACT

An object of the present invention is to provide a method for inhibiting activation of signaling pathway mediated by erbB1 or erbB2 in human cell and a signaling inhibitor to be used therefor. The above-described activation of signaling pathway can be inhibited by a polypeptide comprising at least one of PTB domain or ERK2 binding domain of human FRS2β. The above-described polypeptide may be introduced directly into cell, or nucleic acid which encodes for the above-described polypeptide may be introduced into cell to allow expression of the polypeptide in the cell. Such polypeptide and nucleic acid can be used, for example, as a signaling inhibitor. In addition, since erbB1 and erbB2 are involved in development of cancer, the above-described signaling inhibitor is also useful, for example, as an anticancer drug.

2 Claims, 15 Drawing Sheets

(A)

(B)

(A)

(B)

(E)

(A)

(B)

(C)

(A)

(B)

(A)

(B)

METHOD FOR INHIBITING SIGNAL TRANSDUCTION, SIGNAL TRANSDUCTION INHIBITOR TO BE USED THEREIN AND USE THEREOF

CROSS-REFERENCE TO RELATED APPLICATIONS

This application is a 371 US National Stage application of International Application No. PCT/JP2007/056100, filed Mar. 23, 2007, which claims priority to U.S. Provisional Application No. 60/785,379, filed on Mar. 24, 2006, which is hereby incorporated by reference in its entirety.

TECHNICAL FIELD

The present invention relates to a method for inhibiting signaling, signaling inhibitor to be used therefor and use thereof.

BACKGROUND ART

It has been widely known that receptor tyrosine kinases of signal transduction pathway play a role in the development of cancer. Among them, erbB1 and erbB2 belonging to erbB family and expressed in cell membrane are receptor-type proteins having tyrosine kinase activity, and their overexpression in various types of cancers have been reported. ErbB1 is sometimes referred to as EGFR (epidermal growth factor receptor) or HER1, and its overexpression has been identified, for example, in squamous cell carcinoma such as mouth cancer and esophageal cancer, non-small-cell lung cancer, and the like. ErbB2 is sometimes referred to as HER2 or neu, and its over expression has been identified in breast cancer (10-30%), ovarian cancer (about 30%), bladder cancer (30-40%), and the like. As mentioned above, from the fact that the overexpression of erbB1 or erbB2 plays a role in the development of cancer, antibodies against these receptors have been attempted to be used as a molecular-targeted anticancer drug. A specific example includes an anti-erbB2 antibody (common name: Trastuzumab, trade name: Herceptin) for breast cancer and an anti-erbB1 antibody (common name: Gefitinib, trade name: Iressa) for non-small-cell lung cancer. However, administration of the anticancer drug targeting erbB1 or erbB2 is limited to the case of cancer which expresses the above-described receptors in large excess. Therefore, it has been desired to provide a new anticancer drug.

In addition, on the occasion of deciding on courses of treatment of a patient with breast cancer, as mentioned above, presence or absence of overexpression of erbB2 (HER2) has to be determined in advance. The reason is that the patient to be applied with the above-described anti-erbB2 antibody is limited to the case in which the overexpression of erbB2 is identified. For the method for testing the above-described overexpression of erbB2, Hercep Test has been employed conventionally. This is a method of immunostaining of erbB2 expressed on the surface of cell with monoclonal antibody, in which judgment is made by 4 levels of 0, 1+, 2+ and 3+, and the cases of 2+ and 3+ are evaluated as overexpression. As a detection method for this erbB2, it is desirable to detect the activated erbB2 through tyrosine phosphorylation. However, there is a problem that, when specific detection of phosphorylation site is carried out, other phosphorylated erbB family is also detected. Therefore, there remains a problem that it is not clear whether the signaling pathway works actually by the phosphorylation of overexpressed erbB2. Further, even when erbB2 is expressed in large excess, if the signaling of erbB2 does not function practically, the treatment by anti-erbB2 antibody will be inappropriate. Such a problem lies similarly in the detection of erbB1, in the treatment using the anti-erbB1 antibody, and the like.

Non-patent Literature 1: Oncology, vol. 20, p 1763-1771, 2006.

Non-patent Literature 2: Journal of Clinical Oncology, vol. 25, p 587-595, 2007.

SUMMARY OF THE INVENTION

Problems to be Resolved by the Invention

And so, an object of the present invention is to provide a method for inhibiting activation of signaling pathway mediated by erbB1 or erbB2 in human cell and a signaling inhibitor to be used therefor. In addition, another object of the present invention is to provide an anticancer drug against cancer in which the signaling pathway mediated by erbB1 or erbB2 in human cell is involved, and a method for treating the same. Further, another object of the present invention is to provide a method for determining whether the above-described signaling pathway mediated by erbB1 or erbB2 is in function in human cell.

Means of Solving the Problems

To achieve the above-described objects, the method for inhibiting signaling of the present invention is a method for inhibiting activation of the signaling pathway, wherein the above-described signaling pathway is mediated by erbB1 or erbB2 in human cell; and the above-described activation of the signaling pathway is inhibited by at least one polypeptide selected from the group consisted of the following (A1), (A2), (B1) and (B2):

(A1): a polypeptide consisted of an amino acid sequence comprising the 1st-the 185th region in the amino acid sequence shown in SEQ ID NO: 1;

(A2): a polypeptide consisted of an amino acid sequence in the above-described (A1) in which one or several amino acid residues are deleted, replaced or added, and which has a function equivalent to PTB domain of human FRS2β;

(B1): a polypeptide consisted of an amino acid sequence comprising the 237th-the 252nd region in the amino acid sequence shown in SEQ ID NO: 1;

(B2): a polypeptide consisted of an amino acid sequence of the above-described (B1) in which one or several amino acid residues are deleted, replaced or added, and which has a function of binding with human ERK2.

The signaling inhibitor of the present invention is a signaling inhibitor which inhibits the activation of the signaling pathway mediated by erbB1 or erbB2 in human cell, comprising the first signaling inhibitor and the second signaling inhibitor as shown below.

The first signaling inhibitor comprises nucleic acid, wherein the above-described nucleic acid is at least one nucleic acid selected from the group consisted of the following (a1), (a2), (b1) and (b2), and expresses coded polypeptide thereof in the cell:

(a1): nucleic acid consisted of a nucleotide sequence comprising the 1st-the 555th region of the nucleotide sequence shown in SEQ ID NO: 2;

(a2): nucleic acid consisted of the nucleotide sequence of the above-described (a1) in which one or several nucleotides are deleted, replaced or added, and which encode for a polypeptide having a function equivalent to PTB domain of human FRS2β;

(b1): nucleic acid consisted of a nucleotide sequence comprising the 709th-the 756th region of the nucleotide sequence shown in SEQ ID NO: 2;

(b2): nucleic acid consisted of the nucleotide sequence of the above-described (b1) in which one or several nucleotides are deleted, replaced or added, and encode for a polypeptide having a function of binding with human ERK2.

In addition, the second signaling inhibitor comprises a polypeptide, wherein the above-described polypeptide is at least one polypeptide selected from the group consisted of the above-described (A1), (A2), (B1) and (B2).

The anticancer drug of the present invention is an anticancer drug for humans, which includes the signaling inhibitor of the present invention. In addition, the cell proliferation inhibitor of the present invention includes the signaling inhibitor of the present invention.

The marker of the present invention is a down-regulation marker for the determination of the presence of down-regulation in the signaling pathway, wherein the above-described signaling pathway is mediated by erbB1 or erbB2 in human cell; and the down-regulation marker comprises at least one of human FRS2β and transcript of FRS2β gene.

The measurement kit for the marker of the present invention is a measurement kit for a down-regulation marker of the present invention, which comprises at least one substance selected from the group consisted of a specific antibody for human FRS2β, a specific probe for human FRS2β gene and a specific primer for human FRS2β gene.

The method of treatment of the present invention is a method for treating human cancer, which comprises a step of administration of the signaling inhibitor of the present invention.

The method of determination of the present invention is a method for determining the presence of the down-regulation in the signaling pathway, wherein the above-described signaling pathway is mediated by erbB1 or erbB2 in human cell, which comprises a step of detection of the down-regulation marker of the present invention.

The method of diagnosis of the present invention is a method of diagnosis for making judgment on the necessity of treatment with anticancer drug for human cancer cell, wherein the above-described anticancer drug comprises an anti-human-erbB1 antibody or an anti-human-erbB2 antibody, and the method of diagnosis comprises a step of detection of the down-regulation marker of the present invention.

Effect of the Invention

The present inventors have found, as the results of intensive study, that the FRS2β down-regulates the signaling of erbB1 and erbB2. And further, the present inventors have found that any of polypeptide having at least one of PTB domain (phosphorylated tyrosine binding domain) of FRS2β and a binding domain of FRS2β with ERK2 (extracellular signal regulation kinase 2) (herein after, referred to as "ERK2 binding domain") may cause the above-described down-regulation. It should be noted that the ERK2 binding domain is the one which has been identified by the present inventors.

As mentioned above, according to the polypeptide of the present invention, the above-described signaling pathway may be down-regulated. Therefore, for example, by introducing the polypeptide of the present invention or the nucleic acid capable of expressing the polypeptide of the present invention into an objective human cell, the above-described signaling in the above-described cell can be suppressed. Further, from the fact that the signaling of erbB1 or erbB2 is involved in development of cancer as described above, prevention of development of the cancer and also treatment of the cancer may be performed by way of inhibition of signaling according to the present invention. In addition, since, for example, malignant alteration of cell as well as proliferation of cell can be suppressed by the above-described inhibition of signaling, it can also be said that the present invention is useful for prevention and treatment of cancer.

In addition, because of the fact that the signaling of erbB1 or erbB2 is down-regulated by FRS2β, determination on whether the above-described signaling is working can also be performed by detecting FRS2β in the target cell. And, on the basis of the result of the determination, for example, judgment on the necessity of treatment with anti-erbB1 antibody or anti-erbB2 antibody which inhibits the function of erbB1 or erbB2 can be made. As stated above, it can be said that the present invention is a quite useful technology, for example, in the fields of medical treatment and molecular cytology.

BRIEF DESCRIPTION OF THE DRAWINGS

In FIG. 1, (A) shows photographs of colony morphologies; (B) is a graphical representation of rate (%) of transformed colonies to hygromycin-G418-resistant colonies (100%), in one Example of the present invention.

In FIG. 2, (C) shows photographs representing the results of immunoblotting of cells; (D) is a graphical representation of ratio of expression level of SNT-2 to EGFR (EGFR/SNT-2) in the cell, in another Example of the present invention.

FIG. 3 shows photographs representing the results of immunoblotting in yet another cell of the present invention.

In FIG. 4, (A) shows photographs representing the results of immunoblotting of the cells; (B) shows photographs representing the results of immunoblotting of the cells in yet another Example, in yet another Example of the present invention.

In FIG. 5, (C) shows photographs representing the results of immunoblotting of the cells; (D) shows photographs representing the results of immunoblotting of the cells in yet another Example, in yet another Example of the present invention.

In FIG. 6, (E) shows photographs representing the results of immunoblotting of the cells in yet another Example of the present invention.

In FIG. 7, (A) shows photographs representing the results of immunoblotting of the cells in yet another Example of the present invention.

In FIG. 8, (B) shows photographs representing the results of immunoblotting of the cells; (C) shows photographs representing the results of immunoblotting of the cells in yet another Example, in yet another Example of the present invention.

In FIG. 9, (A) is a schematic diagram showing genes to be inserted into vector.

In FIG. 10, (B) shows photographs representing the results of immunoblotting of the cells in yet another Example of the present invention; (C) shows photographs representing the results of immunoblotting of the cells in yet another Example of the present invention.

FIG. 11 shows photographs representing the results of immunoblotting of the cells in yet another Example of the present invention.

FIG. 12 shows photographs representing the results of immunoblotting of the cells in yet another Example of the present invention.

In FIG. 13, (A) shows photographs representing the results of northern blotting and western blotting; (B) shows photographs representing the results of immunoblotting of the cells, in yet another Example of the present invention.

In FIG. 14, (A) is a graphical representation of cellular change with time; (B) shows photographs representing the results of immunoblotting of the cells, in yet another Example of the present invention.

In FIG. 15, (A) shows photographs representing the shape of colonies; (B) is a graphical representation of number of colonies, in yet another Example of the present invention.

FIG. 16 shows photographs representing the results of immunoblotting of the cells in yet another Example of the present invention.

FIG. 17 shows photographs representing the results of immunoblotting of the cells in yet another Example of the present invention.

BEST MODE FOR CARRYING OUT THE INVENTION

<Method for Inhibiting Signaling>

Figure 1:
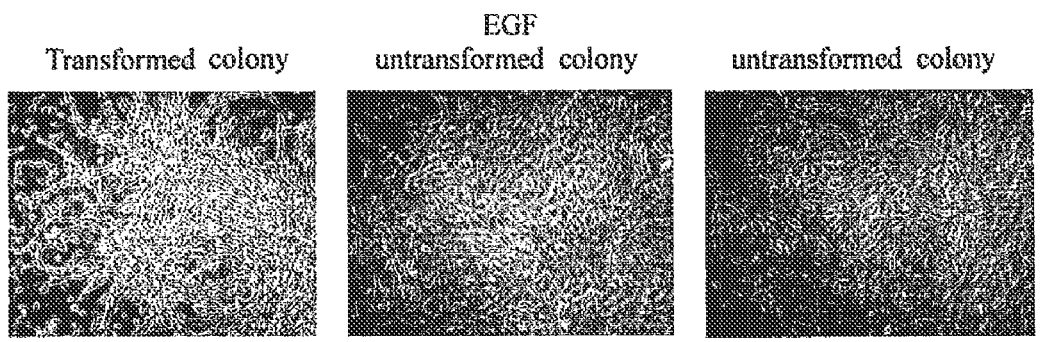
FIG. 1.
Figure 1:
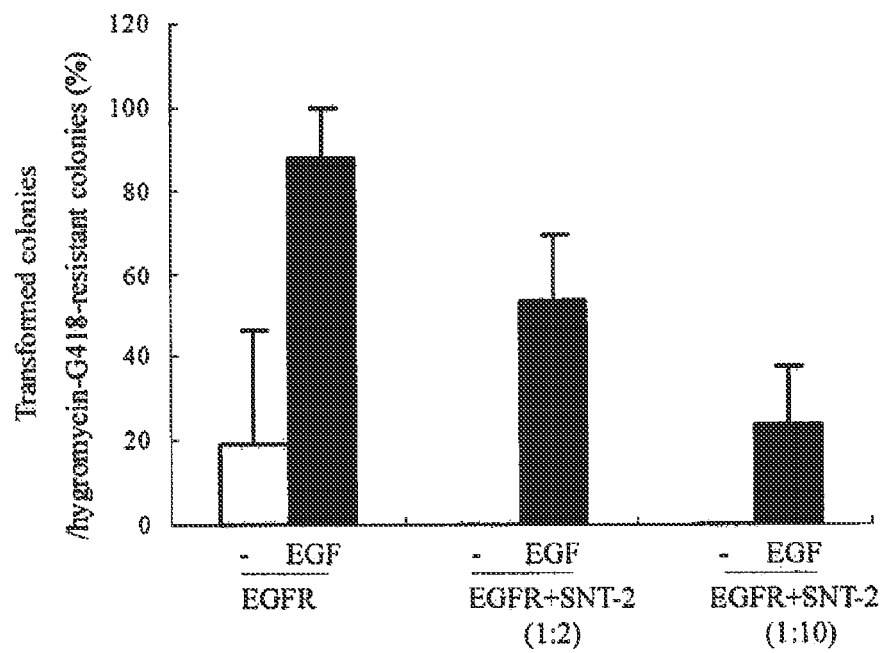

The method for inhibiting signaling of the present invention is a method by which the activation of the signaling pathway is inhibited, wherein the above-described signaling pathway is a signaling pathway mediated by erbB1 or erbB2 in human cell, and the above-described activation of signaling pathway is inhibited by at least one polypeptide selected from the group consisted of the following (A1), (A2), (B1) and (B2).

(A1): A polypeptide consisted of an amino acid sequence comprising the 1st-the 185th region in the amino acid sequence shown in SEQ ID NO: 1.

(A2): In the amino acid sequence of the above-described (A1), the polypeptide is consisted of an amino acid sequence in which one or several amino acid residues are deleted, replaced or added, and which has a function equivalent to PTB domain of human FRS2β.

(B1): A polypeptide consisted of an amino acid sequence comprising the 237th-the 252nd region in the amino acid sequence shown in SEQ ID NO: 1.

(B2): In the amino acid sequence of the above-described (B1), the polypeptide is consisted of an amino acid sequence in which one or several amino acid residues are deleted, replaced or added, and which has a function of binding with human ERK2.

The erbB1 and erbB2 are, as mentioned previously, each receptor-type tyrosine kinases belonging to erbB family that participates in signaling. The former erbB1 is a receptor for EGF (epidermal growth factor) and the like as a ligand. When the above-described ligand acts on the extracellular domain of the above-described erbB1, homodimerization or heterodimerization of the above-described receptor is induced, and then the kinase domain in the intracellular domain of the erbB1 is activated. The erbB1 is sometimes referred to, for example, as EGFR (epidermal growth factor receptor) or HER1. In contrast to erbB1, the erbB2 is a receptor having no specific corresponding ligand. In the above-described ebB2, homodimerization or heterodimerization with other receptor is induced by stimulation from outside, and thereby the kinase domain in the intracellular domain of erbB2 is activated. This erbB2 is sometimes referred to as HER2 or neu.

Human FRS2β is sometimes referred to as SNT-2 or FRS3. FRS2β is a docking protein taking part in signaling of FGFR (fibroblast growth factor receptor) or neutrophine receptor, and the following things have been known. FRS2β is coupled to the lipid of cell membrane through myristylation signal possessed on the N-terminal thereof. And, when the FGFR or neutrophine receptor is activated, FRS2β will bind with the intracellular domain of the above-described receptor through PTB domain (phosphorylated tyrosine binding domain) of the FRS2β. The FRS2β bound with the above-described receptor will further receive phosphorylation of tyrosine residue thereof. When the FRS2β receives phosphorylation, various types of tyrosine phosphatase (e.g., Shp2, Grb and the like) bind to this tyrosine phosphorylation domain, and then these tyrosine phosphatases are activated. And, activation of these tyrosine phosphatases may give rise to, for example, activation of Ras-ERK pathway and the like. However, the FRS2β shows completely different function from that reported for signaling of the above-described FGFR in the signaling of erbB1 or erbB2. And, there is no report on anything about this matter. The fact that, in the signaling of erbB1 or erbB2, FRS2β does not give rise to activation of signaling but to down-regulation was found first by the present inventors as mentioned previously. And, the present inventors have further found that, according to at least one of PTB domain and a domain capable of binding with ERK2 (ERK2 binding domain) in the FRS2β, the above-described down-regulation can be realized. Specifically, down-regulation of signaling is taken place in such a way that, for example, autophosphorylation of erbB1 or erbB2, and phosphorylation of down stream molecules are inhibited.

Amino acid sequence of human FRS2β, the entire sequence of human FRS2β gene and CDS sequence (including stop codon) encoding human FRS2β and the like have been registered, for example, in NCBI Accession No. MN_006653. Amino acid sequence of human FRS2β and CDS sequence of human FRS2β gene are shown in SEQ ID NO: 1 and SEQ ID NO: 2, respectively. The PTB domain of human FRS2β is the $1^{st}$-188th region (SEQ ID NO: 3) in SEQ ID NO: 1, and coding sequence thereof is the 1st-the 555th region (SEQ ID NO: 4) in SEQ ID NO: 2. In addition, the ERK2 binding domain of human FRS2β is the 237th-the 252 nd region (SEQ ID NO: 5) in SEQ ID NO: 1, and coding sequence thereof is the 709th-the 756th region (SEQ ID NO: 6) in SEQ ID NO: 2.

The polypeptide of the present invention may be a polypeptide which has at least one of the functions of a function of PTB domain and a function of binding with human ERK2.

First, the polypeptide having a function of PTB domain includes, for example, the polypeptides shown in the following (A1)-(A2).

(A1): A polypeptide consisted of an amino acid sequence comprising the 1st-the 185th region in the amino acid sequence shown in SEQ ID NO: 1.
(A2): In the amino acid sequence of the above-described (A1), the polypeptide is consisted of an amino acid sequence in which one or several amino acid residues are deleted, replaced or added, and which has a function equivalent to PTB domain of human FRS2β.

In the above-described (A2), the number of amino acid residue which can be deleted, replaced or added is not particularly limited as long as it is within a range of not losing the function of PTB domain of the human FRS2β. The number of amino acid residue acceptable for the above-described deletion and the rest is, for example, preferably 1-4 residues, more preferably 1-3 residues and further preferably 1-2 residues for 50 amino acid residues. In addition, the homology of amino acid sequence to the polypeptide of the above-described (A1) is, for example, 70% or higher.

The polypeptide of the above-described (A1) may be, for example, a polypeptide comprising PTB domain as mentioned previously, or a polypeptide consisted of only PTB domain shown in the following (A3).
(A3): A polypeptide consisted of an amino acid sequence of the 1st-the 185th in the amino acid sequence (SEQ ID NO: 3) shown in SEQ ID NO: 1.

Next, the polypeptide having a function of ERK2 binding domain includes, for example, the polypeptides shown in the following (B1)-(B2).
(B1): A polypeptide consisted of an amino acid sequence comprising the 237th-the 252nd region in the amino acid sequence shown in SEQ ID NO: 1.
(B2): In the amino acid sequence of the above-described (B1), the polypeptide is consisted of an amino acid sequence in which one or several amino acid residues are deleted, replaced or added, and which has a function of binding with human ERK2.

In the above-described (B2), the number of amino acid residue which can be deleted, replaced or added is not particularly limited as long as it is within a range of not losing the function of human ERK2 binding domain. The number of amino acid residue acceptable for the above-described deletion and the rest is, for example, preferably 1-4 residues, more preferably 1-3 residues and further preferably 1-2 residues for 50 amino acid residues. In addition, homology of amino acid sequence to the polypeptide of the above-described (B1) is, for example, 70% or higher.

The polypeptide of the above-described (B1) may be, for example, a polypeptide comprising ERK2 binding domain as mentioned previously, or a polypeptide consisted of only PTB domain shown in the following (B3).
(B3): A polypeptide consisted of an amino acid sequence of the 237th-the 252nd in the amino acid sequence (SEQ ID NO: 5) shown in SEQ ID NO: 1.

The polypeptide in the present invention may be either one of polypeptides of a polypeptide having a function of PTB domain as mentioned previously and a polypeptide having a function of ERK2 binding domain, or may be both polypeptides. In addition, the polypeptide in the present invention may be a polypeptide having both functions of PTB domain and ERK2 binding domain. The above-described polypeptide having functions of both domains includes, for example, polypeptides shown in the following (C1)-(C3). By the way, in the following (C3), the number of amino acid acceptable for deletion and the like is, for example, the same as mentioned previously.

(C1): Human FRS2β consisted of amino acid sequence shown in SEQ ID NO: 1.
(C2): A fused polypeptide comprising at least one polypeptide of the above-described (A1) and (A2) and at least one polypeptide of the above-described (B1) and (B2).
(C3): In the amino acid sequence of the above (C1) and (C2), a polypeptide consisted of an amino acid sequence in which one or several amino acid residues are deleted, replaced or added, and which has functions of both PTB domain and human ERK2 binding domain.

As mentioned previously, in the signaling pathway mediated through erbB1 or erbB2 inhuman cell, down-regulation occurs by the presence of at least one of polypeptide having a function of PTB domain and a polypeptide having a function of ERK2 binding domain. Therefore, in the present invention, a polypeptide having at least one of the domains may be present in the target human cell. For this reason, in the present invention, for example, the nucleic acid which encodes for the above-described polynucleotide is introduced into the target cell, and thereby, the above-described polypeptide may be expressed in the cell, or the polypeptide may be administrated into the target cell. And so, as the first embodiment, introduction of signaling inhibitor comprising nucleic acid; and as the second embodiment, introduction of signaling inhibitor comprising polypeptide; will be each described. It should be noted that these are only for illustration, and the present invention is not limited thereto.

First Embodiment

Administration of Nucleic Acid

The method for inhibiting signaling of the present invention comprises a step of administration of a signaling inhibitor comprising nucleic acid into human cell, wherein the above-described nucleic acid encodes for the above-described polypeptide and expresses the above-described polypeptide in the cell. In this regard, herein after, the signaling inhibitor comprising the above-described nucleic acid is sometimes referred to as "the first signaling inhibitor" of the present invention.

The above-described nucleic acid may be the nucleic acid which encodes for the above-described polypeptide. Type of the nucleic acid is not limited, and it may be, for example, either one of DNA or RNA (mRNA). In addition, the above-described nucleic acid may be, for example, naturally-occurring nucleic acid, or synthesized nucleic acid by means of genetic engineering.

First, the nucleic acid which encodes for a polypeptide having a function of PTB domain includes, for example, the nucleic acid shown in the following (a1)-(a2).
(a1): Nucleic acid consisted of a nucleotide sequence comprising the 1st-the 555th region of the nucleotide sequence shown in SEQ ID NO: 2;
(a2): Nucleic acid consisted of the nucleotide sequence of the above-described (a1) in which one or several nucleotides are deleted, replaced or added, and encoding for a polypeptide having a function equivalent to PTB domain of human FRS2β.

The nucleic acid of the above-described (a1) may be, for example, the nucleic acid comprising coding sequence for the PTB domain as mentioned previously, or the nucleic acid consisted of only a coding sequence for PTB domain shown in the following (a3).

(a3): Nucleic acid consisted of a nucleotide sequence of the 1st-the 555th (SEQ ID NO: 4) in the nucleotide sequence shown in SEQ ID NO: 2.

In the above-described (a2), the number of nucleotide which can be deleted, replaced or added is not particularly limited as long as it is within a range of not losing the function of PTB domain encoded by the nucleic acid. The above-described number of nucleotide is not particularly limited, but is, for example, preferably 1-6 nucleotides, more preferably 1-5 nucleotides, further preferably 1-4 nucleotides, and particularly preferably 1-3 nucleotides for 50 nucleotides.

The nucleic acid shown in the above (a2) may be, as long as it is within a range of not losing the function of PTB domain, for example, the nucleic acid which is capable of hybridizing with the nucleic acid described in the above (a1) under stringent condition, or the nucleic acid which has homology to the nucleic acid described in the above (a1) in 90% or higher. The stringent condition for hybridization includes, for example, the standard condition in the field of relevant art; for example, temperature condition is +/−5° C. of Tm value of the nucleic acid of the above-described (a1), preferably +/−2° C. and more preferably +/−1° C. Specific example of the condition includes, the hybridization in 5×SSC solution, 10×Denhardt solution, 100 μg/ml salmon sperm DNA and 1% SDS, at 65° C., and washing (twice) in 0.2×SSC and 1% SDS, at 65° C. for 10 minutes. In addition, homology is, for example, 90% or higher, preferably 95% or higher, more preferably 97.5% or higher.

Next, the nucleic acid which encodes for a polypeptide having the function of ERK2 binding domain includes, for example, the nucleic acids shown in the following (b1)-(b2).
(b1): Nucleic acid consisted of a nucleotide sequence comprising the 709th-the 756th region of the nucleotide sequence shown in SEQ ID NO: 2;
(b2): Nucleic acid consisted of the nucleotide sequence of the above-described (b1) in which one or several nucleotides are deleted, replaced or added, and encoding for a polypeptide having a function of binding with human ERK2.

The nucleic acid of the above-described (b1) may be, for example, the nucleic acid comprising coding sequence for the ERK2 binding domain as mentioned previously, or the nucleic acid consisted of only a coding sequence for the ERK2 binding domain shown in the following (b3).
(b3): The nucleic acid consisted of a nucleotide sequence of the 709th-the 756th (SEQ ID NO: 6) in the nucleotide sequence shown in SEQ ID NO: 2.

In the above described (b2), the number of nucleotide which can be deleted, replaced or added is not particularly limited as long as the polynucleotide encoded by the nucleic acid is within a range of not losing the function of ERK2 binding domain. The above-described number of nucleotide is, for example, the same as mentioned previously.

The nucleic acid shown in the above (b2) may be, as long as it is within a range of not losing the function of ERK2 binding domain, for example, the nucleic acid which is capable of hybridizing with the nucleic acid described in the above (b1) under stringent condition, or the nucleic acid which has homology to the nucleic acid described in the above (b1) in 90% or higher. The above-described stringent condition is the same as described above, and the preferable range of the above-described homology is also the same as described above.

The above-described nucleic acid may be either one of nucleic acid which encode for a polypeptide having a function of PTB domain as mentioned previously or nucleic acid which encode for a polypeptide having a function of ERK2 binding domain, or may be both nucleic acids. In addition, in the present invention, the above-described nucleic acid may be nucleic acid which encode for a polypeptide (including protein) having functions of both PTB domain and ERK2 binding domain. The latter polypeptide includes, for example, polypeptides shown in the following (c1)-(c3). By the way, in the following (c3), the number of nucleotide corresponding to deletion and the like is, for example, the same as mentioned previously. In addition, it may be the entire length or a partial sequence of human FRS2β gene.
(c1): Human FRS2β gene consisted of a nucleotide sequence shown in SEQ ID NO: 2.
(c2): Chimeric nucleic acid comprising at least one of the nucleic acids of the above-described (a1) and (a2) and at least one of the nucleic acids of the above-described (b1) and (b2).
(c3): Nucleic acid consisted of a nucleotide sequence in the above-described (c1) and (c2) in which one or several nucleotides are deleted, replaced or added, and which encodes for a polypeptide having functions of both human PTB domain and human ERK2 binding domain.

The signaling inhibitor in this embodiment may be one which comprises such nucleic acid as mentioned previously. And, according to the method for introducing the above-described nucleic acid into the target cell, for example, additional substance may be included as appropriate. The above-described method for introducing the nucleic acid is not particularly limited, and the method known in the prior art can be used. A specific example includes, for example, a method of utilizing a vector and a method without using a vector.

In the case where the above-described vector is used, it is preferable that, for example, the above-described signaling inhibitor further comprises an additional vector, and the above-described nucleic acid is linked to the above-described vector. The above-described vector is not limited, but any vector known in the prior art can be used. The above-described vector includes, for example, a nonviral vector and a viral vector, and it is preferable to select a vector which is capable of expressing the above-described nucleic acid in a target cell or in a target living body. The above-described nonviral vector includes, for example, expression vectors such as pGEX-4T-1, pcDNA3.1 (Invitrogen), pZeoSV (Invitrogen), pBK-CMV (Stratagene) and pCAGGS. In addition, the viral vector includes, for example, retrovirus vector, lentivirus vector, adenovirus vector, adeno-associated virus vector (AAV vector), DNA virus and RNA virus such as herpesvirus, Vaccinia virus, poxvirus, poliovirus, sindbisvirus, Sendai virus, SV40 and immunodeficiency virus (HIV). Generally, the above-described nucleic acid may be inserted into the down stream of promoter of these vectors to make the expression thereof possible. In this manner, a recombinant vector produced by insertion of the above-described nucleic acid into a vector can be used as an above-described signaling inhibitor.

The above-described recombinant vector may further comprise a regulatory sequence which regulates expression of the above-described gene. The above-described regulatory sequence includes, for example, constitutive promoters such as cytomegalovirus (CMV)-derived promoter, Rous sarcomavirus (RSV), simian virus-40 (SV-40), muscle β-actin promoter and herpes simplex virus (HSV); tissue-specific promoter such as thymidine kinase promoter; inductive promoter and controlling promoter such as growth-hormone controlling promoter, promoter under regulation of lac operon sequence and zinc-inductive metallothionein promoter. The above-described regulatory sequence may be allocated or coupled to a site where the expression of the above-described gene can be controlled functionally based on the method known in the prior art. In addition to this, for example, enhancer sequence, polyadenylation signal and the sequence of the replication origin (ori) may be comprised.

In addition, the above-described recombinant vector may have a sequence which encodes for a selection marker such as, for example, drug-resistance marker, fluorescent protein marker, enzyme marker, cell-surface receptor marker, and the like.

In the case of a method in which the vector is not used, it is preferable for the above-described signaling inhibitor to comprise further, for example, liposome and particles (metal particles) for gene gun. For example, by incorporating the above-described nucleic acid into the liposome, the nucleic acid in the above-described liposome can be incorporated into the cell. In addition, for example, by shooting the above-described particle coated with the above-described nucleic acid into the cell by a gene gun, the above-described nucleic acid can be transported into the cell. In such case, to make the above-described nucleic acid possible to express the objective polypeptide in the cell, it is preferable to comprise further, for example, regulatory sequence such as promoter.

The method for introducing the signaling inhibitor including the above-described nucleic acid into test subjects is not limited. There are, for example, a method of introducing in vivo the signaling inhibitor directly into the body, and a method in which the above-described signaling inhibitor is introduced ex vivo into the target cell or tissue derived from the test subject, and the cell and the like which has been incorporated with the signaling inhibitor is returned to the body of the test subject.

In the case of the former in vivo method, for example, after an appropriate sterilization treatment, the above-described signaling inhibitor may be introduced into the test subject. The method of introduction is not particularly limited, and the method known in the prior art such as, for example, administration by injection or gene gun, liquid immersion can be employed as appropriate.

In the case of the latter ex vivo method, for example, calcium phosphate method, polyethylene glycol method, lipofection method, electroporation method, ultra sound nucleic acid transfer method, method of introduction by gene gun, DEAE-dextran method, direct infusion method using glass capillary, method using virus vector as mentioned previously are included.

As stated above, if the signaling inhibitor including the above-described nucleic acid is administered into the cell, the polypeptide as mentioned previously will be expressed in the cell. By the expressed polypeptide, the signaling pathway of erbB1 or erbB2 will be down-regulated.

Second Embodiment

Administration of Polypeptide

The method for inhibiting signaling of the present invention comprises a step of administration of a signaling inhibitor including the above-described polypeptide. As stated above, by the direct administration of the above-described polypeptide into the target cell, the signaling pathway of erbB1 or erbB2 can also be down-regulated. In this regard, herein after, the signaling inhibitor including the above-described polypeptide is sometimes referred to as "the second signaling inhibitor" of the present invention.

The above-described polypeptide may be, for example, naturally-occurring polypeptide, or synthesized polypeptide by chemical synthesis. From the viewpoint that easy preparation on a large scale is possible, polypeptides or proteins which can be expressed through the use of recombinant DNA technology is preferable. The method for preparing polypeptide using such recombinant DNA technology is not particularly limited, however, for example, the recombinant vector as mentioned in the above-described first signaling inhibitor may be used. For example, based on a host-vector system, the above-described recombinant vector is introduced into a suitable host, and thereby, the above-described polypeptide can be expressed. The polypeptide obtained by such method is, if necessary, subjected to purification treatment such as, for example, salt precipitation, centrifugal separation and column chromatography, the purified polypeptide recovered can be used as a signaling inhibitor of the present embodiment.

The method for administering the signaling inhibitor including the above-described polypeptide into test subjects is not particularly limited, and the method known in the prior art can be employed. For example, any method can be employed as appropriate depending on the type of the target cell or tissue, and includes, for example, injection, liquid immersion, and the like.

The above-described signaling inhibitor may further comprise liposome or polymer, and the above-described polypeptide may be encapsulated in the above-described liposome, or the above-described polypeptide may be coupled with the above-described polypeptide.

As stated above, by administration of the signaling inhibitor including the above-described polypeptide into the cell, the signaling pathway of erbB1 or erbB2 can be down-regulated.

In the method for inhibiting signaling of the present invention, target human cell is not limited; however, the method is useful for, for example, the cells with overexpression of erbB1 or erbB2. From the fact that the overexpression of erbB1 or erbB2 is linked with carcinogenesis, it is effective to apply the present invention to the cancer cell such as, for example, breast cancer, ovarian cancer, gastric cancer, bladder cancer, oral cancer, esophageal cancer, brain tumor and non-small cell lung cancer. Among them, particularly in the breast cancer, overexpression of erbB2 is known to be involved in the carcinogenesis, and therefore, the present invention is effective for application to the breast cancer cell. In addition, application to the cells which have the potential of developing the above-described cancers, for example, normal cell of breast, ovary, stomach, bladder, oral cavity, esophagus, brain and lung, is also useful. In addition, the target human cell may be the cells collected from living body, or also the cells in the living body.

According to such method for inhibiting signaling of the present invention, signaling of cell can be inhibited. In this way, for example, malignant alteration of the cell by activation of signaling pathway of erbB1 or erbB2, or proliferation of the cell (e.g. cancer cell) can be restrained. It should be noted that the present invention can also be applied to animal and animal cell other than humans (herein after, same as above).

<Signaling Inhibitor>

The signaling inhibitor of the present invention is, as mentioned previously, the inhibitor which is capable of inhibiting activation of the signaling pathway mediated by erbB1 or erbB2 in human cell. The signaling inhibitor of the present invention includes, firstly, as mentioned previously, the first signaling inhibitor comprising nucleic acid. The above-described first inhibitor may comprise a nucleic acid which encodes for at least one of polypeptide having a function of the above-described PTB domain and a polypeptide having a function of ERK2 binding domain, and expresses it in the cell. The first signaling inhibitor comprising such nucleic acid is as mentioned previously. Next, the signaling inhibitor of the present invention includes the second signaling inhibitor comprising the polypeptide as mentioned previously. The above-described second inhibitor may comprise at least one of polypeptide having a function of the above-described PTB domain and a polypeptide having a function of ERK2 binding domain. The second signaling inhibitor comprising such polypeptide is as mentioned previously.

According to the signaling inhibitor of the present invention, signaling of cell can be inhibited. In this way, for example, malignant alteration of the cell by activation of signaling pathway of erbB1 or erbB2, or proliferation of the cell (e.g. cancer cell) can be restrained. Therefore, the signaling inhibitor of the present invention is useful, for example, as an anticancer drug or a cell proliferation inhibitor.

<Method for Treating Cancer>

Method of treatment of the present invention is a method for treating human cancer, and comprises a step of administration of the signaling inhibitor of the present invention. The method of treatment of the present invention is characterized by the use of the signaling inhibitor of the present invention itself, and other processes and conditions are not limited. The method for administering the signaling inhibitor of the present invention is, for example, the same as mentioned previously. In addition, the cancer to which the present invention is applied preferably is, for example, the one in which the signaling pathway of erbB1 or erbB2 is involved, and, for example, breast cancer, ovarian cancer, gastric cancer, bladder cancer, oral cancer, esophageal cancer, brain cancer and non-small cell lung cancer are included. In addition, application to the cells having a potential of developing the above-described cancer, for example, the normal cell of breast, ovary, stomach, bladder, oral cavity, esophagus, brain and lung, is also useful. It should be noted that the method of treatment of the present invention also comprises, for example, prevention of malignant alteration.

<Anticancer Drug>

Anticancer drug of the present invention is an anticancer drug for human use, and comprises the signaling inhibitor of the present invention. The anticancer drug of the present invention may comprise the above-described signaling inhibitor, and its form is not limited. In addition, method of its usage and the like are also the same as described above.

As mentioned previously, it has been known that the overexpression of erbB1 or erbB2 which are receptors of signaling pathway is involved in the malignant alteration. Therefore, the anticancer drug comprising the signaling inhibitor of the present invention is useful for the treatment of the cells which overexpress erbB1 or erbB2, or cancer cells in which these signaling pathways are involved. The above-described cancer cells include, for example, breast cancer, ovarian cancer, gastric cancer, bladder cancer, oral cancer, esophageal cancer, brain cancer and non-small cell lung cancer. In addition, application to cell which has a potential of developing the above-described cancer, for example, normal cell of breast, ovary, stomach, bladder, oral cavity, esophagus, brain, lung, and the like is also useful. It should be noted that the anticancer drug of the present invention also includes, for example, preventive agent for malignant alteration.

<Cell Proliferation Inhibitor>

Cell proliferation inhibitor of the present invention comprises the signaling inhibitor of the present invention. The cell proliferation inhibitor of the present invention may comprise the above-described signaling inhibitor, and its form is not limited. In addition, method of its usage and the like are also the same as described above. In addition, the cells to which the cell proliferation inhibitor of the present invention is applied are not limited; however, the cells include the cancer cells or normal cells as described above.

<Marker>

Marker of the present invention is, as mentioned previously, the marker for determining presence of down-regulation in the signaling pathway, wherein the above-described signaling pathway is mediated by erbB1 or erbB2 in human cell; and the marker comprises at least one of human FRS2β and transcription product of FRS2β gene.

As mentioned previously, it has been clarified by the inventors that human FRS2β down-regulates both signaling pathways of erbB1 and erbB2. Therefore, by determining the presence of expression or the expression level of human FRS2β in the target human cell, judgment on whether the above-described signaling pathway is down-regulated or not can be made. The similar judgment can also be made by the presence of transcript or transcript level (e.g., amount of mRNA) of human FRS2β gene. In a specific example, for example, using the FRS2β-mRNA/GAPDH-mRNA value of $1,452 \times 10^{-2}$ as a cutoff value, the judgment on the presence of down-regulation can be made.

Further, by making judgment on the presence of down-regulation, the following things will become possible. (1) As mentioned previously, it has been known that the overexpression of erbB1 or erbB2 and the activation of overexpressed erbB1 or erbB2 plays a role in the malignant alteration. Therefore, if detection of the marker of the present invention in human cell is carried out and judgment on the presence of down-regulation is made, for example, risk of malignant alteration of the human cell can be determined. That is, when the down-regulation is taken place, it can be determined that possibility of malignant alteration attributable to the above-described signaling pathway is low; and when the down-regulation is not taken place, it can be determined that there is a possibility of malignant alteration attributable to the above-described signaling pathway. (2) If the detection of the marker of the present invention for human cell is carried out and judgment on the presence of down-regulation is made, it can be determined whether the malignant alteration of the above-described cancer cells is attributable to the above-described signaling pathway or attributable to other mechanism. (3) Further, as stated in the above (2), if the judgment on whether the cause of the malignant alteration is attributable to the above-described signaling pathway is made, therapeutic strategy of the cancer can also be decided. As an example, the therapeutic strategy of breast cancer will be described. In about 10-30% of breast cancer patients, overexpression of erbB2 has been identified, and as an effective anticancer drug for such patients, the above-described anti-erbB2 antibody which is capable of inhibiting the function of erbB2 has been used. However, when the signaling of erbB2 has already been down-regulated by FRS2β, the signaling of erbB2 is thought to be not involved in the malignant alteration, administration of the anti-erbB2 antibody targeting erbB2 cannot be an appropriate treatment. And so, detection of the marker of the present invention for the breast cancer cell of the patient and determination of the presence of down-regulation are carried out, and thereby, judgment can be made on whether the treatment by anti-erbB2 antibody is appropriate. (4) In addition, with respect to breast cancer, Hercep Test which detects erbB2 overexpression as mentioned previously has been carried out. However, while phosphorylation of erbB2 is needed to be detected in this test, other erbB family is also detected. Therefore, there remains a problem of difficulty in determining whether the signaling of erbB2 is actually working. In contrast to this, if the marker of the present invention is detected and determination of the presence of down-regulation is carried out, it is possible to detect whether the signaling of erbB2 is actually working, instead of erbB2 itself.

The amino acid sequence of human FRS2β and the nucleotide sequence of human FRS2β gene have been registered in NCBI Accession No. MN_006653. As the above-described marker, for example, transcription product (mRNA) of human FRS2β gene is preferable, and measurement on presence of the transcript of the above-described mRNA or amount of the transcript is preferable.

<Method for Measuring Marker>

Measurement of the marker of the present invention is not limited, and can be determined suitably depending on the type of the marker.

(1) Measurement of Human FRS2β

When the above-described marker of the present invention is human FRS2β, methods of measurement known in the prior art for detection of particular polypeptide or protein can be employed. The above-described method of measurement is not limited in any way. Specific example includes, for example, immunoassay method using antibody. The above-described immunoassay method includes, for example, enzyme-linked immunosorbent assay (ELISA) method, immunoagglutination method such as latex immunoagglutination method, immunonephelometry such as latex immunonephelometry, radioimmunoassay, and western blotting method. Among them, as an above-described immunoassay method, ELISA is preferable. The above-described ELISA includes, for example, sandwich ELISA method and competitive ELISA method.

In the case where human FRS2β is measured by immunoassay, an antibody for detection includes, for example, anti-human FRS2β antibody. The above-described anti-human FRS2β antibody may be prepared, for example, by the method known in the prior art. To give a specific example, for example, an animal is immunologically sensitized by inoculation of human FRS2β as an antigen, polyclonal or monoclonal anti-human FRS2β antibody can be obtained. Animal species of host cell to be sensitized immunologically is not particularly limited, and for example, human, mammal other than human such as rabbit, rat, mouse, goat, sheep, horse, pig, guinea pig, and the like, avian species such as chicken, pigeon, duck, quail, and the like can be used. In addition, the method for inoculating antigen to an animal is also not particularly limited and intradermal administration, subcutaneous administration, intraperitoneal administration, intravenous administration, intramuscular administration, and the like can be employed. The class of immunoglobulin about the antibody obtained in this way is generally IgM and IgG. The antibody obtained can be used, for example, as it is, and further, active fragment of the antibody such as Fab, Fab', $F(ab')_2$ obtained by enzymatic treatment can also be used as an antibody.

The measurement of human FRS2β will be explained by taking an example. It should be noted that the present invention is not limited thereto.

That is, the method for measuring the marker of the present invention comprises the following steps (1) and (2), wherein the above-described marker comprises FRS2β as mentioned previously:

(1) the step in which, anti-human FRS2β antibody against the above-described human FRS2β is added to a biological sample, and then the above-described human FRS2β in the above-described biological sample is allowed to bind with the above-described anti-human FRS2β antibody to form a complex;

(2) the step of measurement of the above-described complex.

Due to excellence in handling, the above-described antibody is preferably fixed (adsorbed) on a plate (for example, ELISA plate), for example, prior to the above-described step (1). In this case, by adding a biological sample to the above-described plate, the above-described complex can be formed in the above-described plate. In the above-described step (2), the method for measuring the above-described complex is not particularly limited. To give a specific example, a method of measurement in which the antigen (human FRS2β in the biological sample) in the above-described complex is further bound with a labeled anti-human FRS2β antibody, and then the above-described labeled antibody is measured, is included (sandwich immunoassay method). The above-described labeling is not particularly limited, and includes, for example, the labeling known in the prior art such as enzyme labeling, fluorescence labeling and radioisotope labeling. Among them, as a labeled antibody, enzyme-labeled antibody is preferable.

An example of sandwich ELISA method using enzyme as a labeling substance will be explained. First, human cell to be a target of diagnosis is collected. And, protein is extracted from the above-described cell to prepare extraction fraction. On the other hand, anti-human FRS2β antibody against human FRS2β of measurement object is prepared, and then immobilized to a measuring container. Then, the above-described extraction fraction is added to the above-described measuring container. Thereby, the immobilized antibody is reacted with the antigen (human FRS2β) in the above-described extraction fraction, and both of them are coupled. After washing the above-described measuring container, the enzyme-labeled antibody (labeled anti-human FRS2β antibody) is added. In this way, the antigen coupled to the above-described immobilized antibody is reacted with the above-described labeled antibody, and both of them are coupled, and thereby a complex with a configuration in which the above-described antigen is sandwiched between two antibodies is formed. And, after the labeled antibody which is not coupled with the above-described antigen is removed, activity of the labeling substance (enzyme) in the above-described complex is measured. This enzyme activity is proportional to the amount of the above-described complex, and in consequence, this shows the amount of antigen of the measurement object in the above-described extraction fraction. The enzyme described above is not limited in any way, and, for example, peroxidase, alkaline phosphatase or β-galactosidase can be used. The two kinds of antibodies used in this method preferably have, for example, different binding sites from each other for the same antigen.

(2) Measurement of Transcription Product (mRNA) of Human FRS2β

In the case where the above-described marker of the present invention is transcription product of human FRS2β, for example, the presence of the transcript mRNA or transcription level may be measured. For the method of such measurement, those known in the prior art can be employed. Specific example includes, for example, a nucleic acid amplification method using specific primer and a method using detection probe. The former includes, for example, PCR method, reverse transcription PCR method and real-time PCR; the latter includes, for example, Southern blotting method and Northern blotting method. It should be noted that, the sequence of the specific primer and the detection probe can be decided as appropriate based on the sequence of human FRS2β gene and mRNA.

In the case where the transcript mRNA is measured, generally, the reverse transcription PCR method or the real-time PCR method has been widely used. In these procedures, for example, cDNA is synthesized by the reverse transcription PCR method using total RNA or mRNA expressed in a biological sample as a template, and then the objective sequence is amplified by the real-time PCR method using the above-described cDNA as a template. In this way, amount of the objective mRNA which has been expressed in the above-described biological sample can be measured. Therefore, in the present invention, for example, in addition to the mRNA of human FRS2β gene expressed in a biological sample, cDNA synthesized by genetic engineering procedure such as PCR and amplified objective sequence (amplified DNA product) can also be referred to as the marker. In this regard, the cDNA to be synthesized using total RNA or mRNA as a template is not particularly limited, and may comprise, for example, an entire length of cDNA of human FRS2β gene or a partial sequence thereof. In addition, the objective sequence to be amplified using cDNA as a template may be, for example, an entire length of cDNA for human FRS2β, or a partial cDNA sequence.

<Measurement Kit for Marker>

The kit for measuring the marker of the present invention includes a first kit for measuring the marker comprising the above-described human FRS2β, and a second kit for measuring the marker comprising a transcript of the above-described human FRS2β gene. The above-described first kit comprises antibody specific for human FRS2β. The above-described antibody is the same as mentioned previously. In addition, the second kit comprises at least one selected from the group consisted of a probe specific for human FRS2β gene and a primer specific for human FRS2β gene. The above-described probe and primer are the same as mentioned previously.

As mentioned previously, by detecting the marker of the present invention, the down-regulation of signaling pathway can be determined. Therefore, the kit for measuring the marker of the present invention can also be referred to as a kit for determining presence of down-regulation of signaling pathway mediated by erbB1 or erbB2 in human cell. In addition, the kit for measuring the marker of the present invention can also be referred to as a kit for determining, from presence or absence of down-regulation, necessity of treatment for human cancer cell with an anticancer drug comprising anti-human erbB1 antibody or anti-human erbB2 antibody.

<Method for Diagnosis>

The method for diagnosis of the present invention is to determine necessity of treatment for human cancer cell with and anticancer drug comprising anti-human erbB1 antibody or anti-human erbB2 antibody, which comprises a step of detecting the marker of the present invention. As mentioned previously, for a cancer in which overexpression of erbB1 or erbB2 is causative, for example, anti-erbB1 antibody or anti-erbB2 antibody has been used as a molecular-targeted anticancer drug. However, when the signaling pathway of erbB1 or the signaling pathway of erbB2 has already been down-regulated by FRS2β, administration of the molecular-targeted anticancer drug cannot be a suitable method of treatment. And so, detection of the marker and the determination of the presence of down-regulation are carried out, and thereby, judgment on the necessity of treatment with molecular-targeted anticancer drug can be made.

<Use of Nucleic Acid and Polypeptide>

The present invention is use of at least one nucleic acid selected from the group consisted of the above-described (a1), (a2), (b1) and (b2) for inhibiting the activation of signaling pathway mediated by erbB1 or erbB2 in human cell. In addition, the present invention is use of at least one nucleic acid selected from the group consisted of the above-described (a1), (a2), (b1) and (b2) for treating human cancer. In addition, the present invention is use of at least one polypeptide selected from the group consisted of above-described (A1), (A2), (B1) and (B2) for inhibiting the activation of signaling pathway mediated by erbB1 or erbB2 in human cell. In addition, the present invention is use of at least one polypeptide selected from the group consisted of the above-described (A1), (A2), (B1) and (B2) for treating human cancer.

In the next place, an Examples of the present invention will be described. In this regard, however, the present invention is not limited in any way by the following Examples.

Example 1

Effect of FRS2β on the signaling of erbB1 was determined. Hereinafter, FRS2β is referred to as "SNT-2" and erbB1 as "EGFR".

(Preparation of Recombinant Vector)

The cDNAs which encode for the entire length of human SNT-2 and for variant SNT-2 were each linked to vectors, and human SNT-2 expression vector and variant SNT-2 expression vector were prepared (Literature 1). The above-described vector used was a plasmid vector having neomycin resistance gene, and having capability of adding AG-tag on the C-terminal. The expression vector linked with coding sequence for the entire length of human SNT-2 is referred to as SNT-2 expression vector. In addition, expression vectors linked with coding sequence of various types of C-terminal-cut-off variant of human SNT-2, namely, polypeptides consisted of the 1st-the 185th region, the 1st-the 202nd region, the 1st-the 219th region, the 1st-the 236th region and the 1st-252nd region in the SEQ ID NO: 1, were prepared. These are referred to as expression vector of C-terminal-cut-off variant, and these are each referred to as 1-185 expression vector, 1-202 expression vector, 1-219 expression vector, 1-236 expression vector and 1-252 expression vector, respectively. In addition, expression vectors linked with coding sequence of various types of internal deletion variant of human SNT-2, namely, polypeptides having deletion of the 186th-the 252nd (Δ 186-252) and deletion of the 237th-the 252nd (Δ 237-252) in the SEQ ID NO: 1 were prepared. These are referred to as expression vector of internal deletion variant, and these are each referred to as Δ 186-252 expression vector and Δ 237-252 expression vector. In addition, expression vector linked with coding sequence of N-terminal-cut-off variant of human SNT-2, namely, polypeptides consisted of the 186th-the 328th region in the SEQ ID NO: 1 is referred to as 186-328 expression vector. In addition, the cording sequence for the entire length of SNT-2 or the cording sequence for Δ 237-252 variant, and FLAG-tag of C-terminal were linked to a retrovirus vector of pMXs-puro vector (Literature 2). These are referred to as SNT-2 expression retrovirus vector, and Δ 237-252 expression retrovirus vector. The objective polypeptides expressed from these vectors are attached with FLAG-tag on their C-terminal.

Literature 1: Huang, L. et al., Biochem. Biophys. Res. Commun. 324: 1011-1017 (2004)

Literature 2: Kitamura, T. et al., Exp. Hematol. 31: 1007-1014 (2003)

Coding sequences of cDNA of wild-type human EGFR and variant thereof were prepared (Literature 3). The above-described variant is a variant in which tyrosine residues in EGFR at the 992nd, the 1068th, the 1086th, the 1148th and the 1173rd were replaced by phenylalanine (herein after, referred to as "F5"). The EGFR coding sequence and the variant coding sequence were linked to vectors having a hygromycin resistance cassette. The expression vector linked with EGFR coding sequence is referred to as EGFR expression vector, and the expression vector linked with F5 coding sequence is referred to as F5 variant expression vector.
Literature 3: Okutani, T. et al., J. Biol. Chem. 269: 31310-31314 (1994)

The cDNA of C-terminal region of SNT-2 (SNT-2-C: the 333rd-the 492nd region in the SEQ ID NO: 1) was linked to pGEX-4T-1, and GET-SNT-2-C expression vector which expresses GST (glutathione S-transferase) fusion protein was prepared (Literature 1). In addition, the cDNA of human ERK2 was linked to pGEX-4T-1, and GST-ERK2 expression vector which expresses GST fusion protein was prepared (Literature 1). From these expression vectors, respective fusion proteins of GST with SNT-2-C and of GST with ERK2 were expressed.

The cDNA of CAMEK1 which is a constantly-active variant of MEK1 (produced by Stratagene) was linked to pCMV vector (produced by Stratagene), and CAMEK1 expression vector was prepared. The CAMEK1 is a variant of MEK1 in which serine (S) at the 218th and the 222nd in MEK1 is replaced by glutamic acid (E).

(Cell Culture)

Saos-2 cell, HEK293 cell, human embryonic lung epithelial cell WI38-VA13, neuroblastoma cell SH-SY5Y and glioblastoma cell T98G were cultured using Dulbecco's modified Eagle's medium (DMEM) containing 10% fetal bovine serum (FBS), at 37° C., under the condition of 5% $CO_2$. Lung cancer cell PC10, LK2, H520, H157, PC14, PC3 and H322 were cultured using RPMI containing 10% fetal bovine serum (FBS), at 37° C., under the condition of 5% $CO_2$. NIH 3T3 cell was cultured using DMEM containing 5% new born calf serum (NBCS), at 37° C., under the condition of 5% $CO_2$.

To attain stable gene transfection, Saos-2 cells were seeded to give $1\times10^6$ cells/100 mm dish, and 0.5 µg of plasmid vector was transfected by standard calcium precipitation method (Literature 4). And, after 48 hours, 400 µg/ml of G418 (produced by Calibiochem) was added, and further cultured for 2 weeks. In addition, HEK293 cells were seeded, for use in transient transfection, to give $2\times10^6$ cells/60 mm dish, and 4 µg of plasmid was transfected using LipofectAMINE® 2000 (produced by Invitrogen) according to the attached protocol.
Literature 4: Chen, C. et al., Mol. Cell. Biol. 7: 2745-2752 (1987)

(Retrovirus-Mediated Gene Expression)

First, packaging cell Plat-E was cultured in DMEM containing 10% FBS. The cultured cells were seeded to give $5\times10^6$ cells/100 mm dish, and 3 mg of plasmid vector was transfected using FuGENE6 (produced by Roche) according to the attached protocol. After 24 hours, culture medium was changed to fresh one, and supernatant containing retrovirus was recovered, and added to NIH 3T3 cell expressing EGFR after 48 hours of culture. And, after culturing for 24 hours, 1.6 µg/ml of puromycin was added, and cultured for another 3 days.

(Antibody)

Anti-EGFR antibody, anti-ERK2 antibody (monoclonal D-2 and polyclonal K-23), anti-H-Ras antibody, anti-GST antibody, horseradish peroxidase (HRP)-labeled anti-mouse IgG antibody and HRP-labeled anti-rabbit IgG antibody were purchased from Santa Cruz Biotechnology. Anti-FLAG M2 monoclonal antibody was purchased from Sigma-Aldrich. Anti-pERK antibody, anti-pMEK antibody, anti-pShc antibody, anti-pPLCg antibody, anti-pJNK antibody, anti-JNK antibody, anti-pp38 MAPK antibody and anti-p38 MAPK antibody were purchased from Cell Signaling Technology. Anti-Shc antibody was purchased from BD Biosciences, anti-phosphotyrosine antibody was from Biotech Co., Ltd and anti-Actin antibody was from Chemicon International Serological, Inc.

As to anti-SNT-2 antibody, a polypeptide comprising the 292nd-the 311th region in the amino acid sequence of human SNT-2 was synthesized, and was conjugated with KLH-MBS, and then used for immunization of rabbit. In addition, the purified GST-SNT-2-C was mixed with FCA (Freund's Complete Adjuvant, only for the first immunization) or with FIA (Freund's Incomplete Adjuvant, for the following 3 immunizations), and used for immunization of rabbit. Two types of rabbit sera obtained were subjected to affinity purification, and used as an anti-SNT-2-P antibody and anti-SNT-2-C antibody. In addition, some anti-SNT-2-C antibodies were biotinylated using EZ-Link Sulfo-NHS-LC-Biotinylation Kit (produced by Pierce Chemical Co.) according to the attached protocol.

(Transformation Assay)

Subclonal NIH 3T3 cell line which shows very low expression level of EGFR was selected (Literature 5, Literature 6), and into this NIH 3T3 cell, the above-described EGFR expression vector, a vector with no gene linkage (herein after, referred to as "control vector"), or SNT-2 expression vector was transfected. The gene transfected cells were grown in DMEM containing 5% NBCS in the presence or absence of EGF (10 ng/ml), then resistant cell line was selected using hygromycin (200 µg/ml, for the selection of EGFR) and G418 (200 µg/ml). The above-described medium was changed every 2 days. Three weeks later, the number of hygromycin-G418 resistant colony and the number of transformed colony were counted (Literature 5).
Literature 5: Gotoh, N. et al., Biochem. Biophys. Res. Commun. 186: 768-774 (1992)
Literature 6: Gotoh, N. et al., Proc. Natl. Acad. Sci. USA 91: 167-171 (1994)

(Ras Activity Assay)

Ras activation assay kit (produced by Upstate Biotechnology) was used according to the attached protocol. Stable gene transfectant of Saos-2 cell was kept serum deficiency state for 24 hours, and then was stimulated with EGF. And, the cell lysate was incubated together with GST-RBD agarose at 4° C. for 30 minutes. For the total cell lysate, namely the solubilized preparation of cell, and the protein which bound to the above-described agarose, immunoblotting was carried out using anti-H-Ras antibody.

(In Vitro Binding Assay)

*Escherichia coli* BL21 having the above-described GST expression vector or the above-described GST-ERK2 expression vector was grown in a Luria Bertani (LB) medium containing 50 µg/ml ampicillin, and then incubated together with 0.5 mM isopropyl-thiogalactopyranoside (IPTG) at 28° C. for 3 hours. The bacterial cells having induced GST fusion protein (GST-ERK2 fusion protein) were lysed, and the cell lysate was incubated together with Glutathione Sepharose beads (produced by GE Healthcare Life Sciences) at 4° C. for 1 hour (Literature 1).

Into HEK293 cell, SNT-2 expression vector or C-terminal-cut-off variant expression vector was transfected, and the cell obtained were solubilized by treating with binding buffer at 4° C. for 10 minutes. Composition of the above-described binding buffer (pH 7.5) was 20 mM Hepes, 150 mM NaCl, 1 mM EDTA, 1% TritonX-100, 5% glycerol, 10 mM pyrophosphoric acid, 1 mM Na3VO4, 1 mM phenylmethylsulfonyl fluoride (PMSF), 5 mg/ml aprotinin and 5 mg/ml leupeptin. The cell-solubilized solution recovered by centrifugation was mixed at 4° C. for 2 hours with the above-described Glutathione Sepharose beads on which the above-described GST fusion protein (GST-ERK2 fusion protein) has been immobilized. Protein was extracted with 1× sample buffer, and then subjected to sodium dodecyl sulfate polyacrylamide gel electrophoresis (SDS-PAGE). And, immunoblotting was carried out using anti-GST antibody, anti-ERK2 antibody and anti-FLAG M2 antibody.

(Immunocoprecipitation Assay)

Before EGF treatment, Saos-2 cell or HEK293 cell was kept serum deficiency state for 24 hours. The cells were solubilized using above-described binding buffer, and cell-solubilized solution was incubated with polyclonal anti-EGFR antibody at 4° C. for 1 hour and further incubated with protein A-Sepharose (produced by Amersham Biosciences) for 1 hour. For the immunoprecipitate, immunoblotting was performed using monoclonal anti-FLAG M2 antibody and anti-EGFR antibody.

(Northern Blotting)

From mouse brain and NIH 3T3 cell, RNA was prepared using standard method (Literature 7). As to probes for mouse FRS2α gene and mouse FRS2β gene, the probes described in a paper were used (Literature 8).

Literature 7: Gotoh, N. et al., Mol. Cell. Biol. 25: 4105-4116 (2005)

Literature 8: Gotoh, N. et al., FEBS Lett. 564: 14-18 (2004)

(Cell Growth Assay)

In the presence or absence of SNT-2, or in the presence or absence of Δ 237-252, NIH 3T3 cells expressing EGFR were seeded to give 2×104 cells/35 mm dish in DMEM medium containing 1% NBCS. After that, the above-described medium was changed into the same medium containing 1% NBCS, except with or without EGF. Further, on every 2 days, the medium was renewed. And, from 2 days after EGF treatment, the number of cells was counted every day.

(Soft Agar Colony-Forming Assay)

In the presence or absence of SNT-2, or in the presence or absence of Δ 237-252, NIH 3T3 cells expressing EGFR were suspended to give 5×104 cells/35 mm dish in DMEM medium containing 10% NBCS and 0.36% agarose. And then, this suspension was plated on a cell culture dish matted with bottom agar layer containing 0.72% agarose. Three weeks later, colonies of over 0.1 mm in diameter were counted.

1. Suppression of Transforming Activity by SNT-2

Using NIH 3T3 cell line which does not express endogenous EGFR, transformation assay was carried out (Literature 5, Literature 6).

As mentioned previously, the above-described EGFR expression vector having a hygromycin resistance cassette and the above-described human SNT-2 expression vector having neomycin resistance cassette were prepared. And, by the transfection of above-described EGFR expression vector exclusively into the above-described NIH 3T3 cell, or by the transfection of the above-described EGFR expression vector together with the above-described SNT-2 expression vector into the above-described NIH 3T3 cell, the above mentioned transformation assay was carried out. It should be noted that, on the occasion of transfecting the above-described EGFR expression vector together with the SNT-2 expression vector, the ratio of the vectors to be transfected was set to 1:2 or 1:10.

The results of transformation assay were shown in FIG. 1. FIG. 1 (A) shows photographs representing morphology of transformed colony and non-transformed colony. In this figure, left hand photograph shows transformed colony; center shows non-transformed colony cultured in the presence of EGF; and right hand photograph shows untransformed colony cultured in the absence of EGF. FIG. 1 (B) shows a graphical representation of rate (%) of transformed colonies to hygromycin-G418-resistant colonies (100%). Measurement was conducted 3 times, and the results are shown by mean±s.d. In the figure, "−" shows the result of no EGF-stimulation; and "EGF" shows the result of EGF-stimulation. In addition, in the figure, (1:2) and (1:10) are the ratios of EGFR expression vector and SNT-2 expression vector transfected into NIH 3T3.

As shown in FIG. 1 (B), when EGF-stimulation was not applied, several transformed colonies were observed in the cells which express EGFR exclusively. However, when EGF-stimulation was not applied, no transformed colony was observed for the cells which express EGFR together with SNT-2. In addition, when EGF-stimulation was applied, transformed colonies were observed at high rates (87%) in the cells which express EGFR exclusively. In contrast, in the cells which express EGFR together with SNT-2, the rate of colony formation of the transformant was decreased (53%, 24%). In addition, depending on the increase in the ratio of the SNT-2 expression vector transfected into NIH 3T3, rate of the transformed colony was decreased.

Further, expression level of EGFR and FLAG-tagged SNT-2 in the transformed colonies and the non-transformed colonies were determined. Firstly, the cell lysate was prepared for the cells of each colony, and immunoblotting assay was carried out using anti-EGFR antibody (produced by Santa Cruz Biotechnology) and anti-FLAG antibody (trade name: Anti-FLAGM2 monoclonal antibody; produced by Sigma-Aldrich). And, using NIH image software, expression level was measured, and the ratio of expression level of EGFR to SNT-2 (EGFR/SNT-2) was calculated. These results were shown in FIG. 2 (C).

Figure 2:
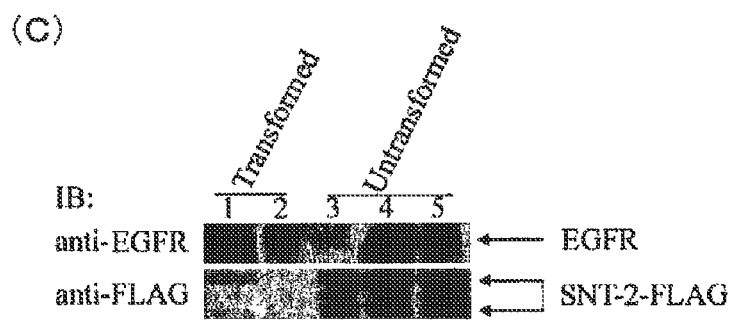
FIG. 2.
Figure 2:
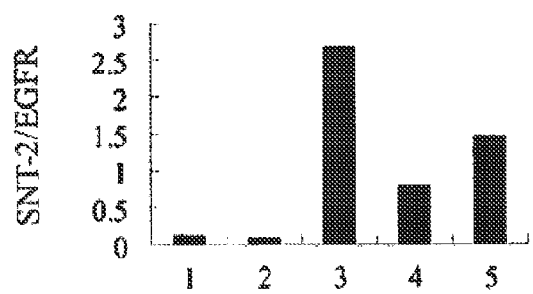

FIG. 2 (C) shows photographs representing the results of immunoblotting of cells in the transformed colony and untransformed colony. FIG. 2 (D) shows a graphical representation of ratio of expression level of SNT-2 to EGFR (EGFR/SNT-2) in the 5 colony cells shown in FIG. 2 (C). As shown in FIG. 2, it was confirmed that expression level of SNT-2 in the untransformed colony cell was high as compared with that in the transformed colony cell. From this result, it turns out that SNT-2 suppresses transforming activity of EGFR.

2. Down-Regulation of Expression Level of SNT-2 in Tumor Cell Lines

Expression level of SNT-2 in the normal brain tissue was compared with that in 2 types of cell lines derived from brain tumor. In addition, expression level of SNT-2 in a cell line derived from normal lung tissue was compared with that in 7 types of cell lines derived from lung cancer. The expression level of SNT-2 was determined by immunoblotting assay using anti-SNT-2-C antibody. The above-described anti-SNT-2-C antibody is an antibody against the C-terminal region of SNT-2 (SNT-2-C) as mentioned previously. In addition, as a control, detection of actine was carried out using anti-actine antibody.

Figure 3:
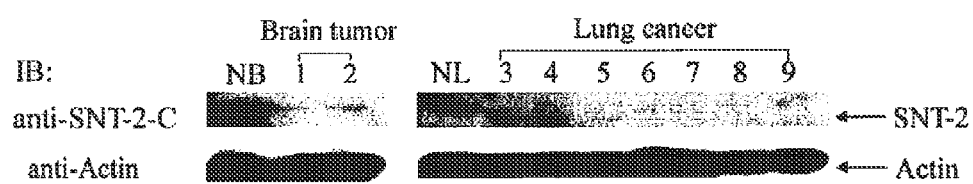
FIG. 3.

The results were shown in FIG. 3. The FIG. 3 shows photographs representing the results of immunoblotting of normal tissues and cell lines derived from cancer. In this figure, NB is normal brain tissue, and 1 and 2 are cell lines derived from brain tumor (1: T98G; 2: SH-SY5Y). In the same figure, NL is normal lung tissue (WI38VA13 derived from normal fetal lung epithelium), and 3-9 are cell lines derived from lung cancer (3: PC10; 4: LK2; 5: H520; 6: H157; 7: PC14; 8: PC3; 9: H322). As shown in this figure, compared with the normal tissues, all of cell lines derived from brain cancer and lung cancer showed low level expression of SNT-2. From this result, it is suggested that SNT-2 might play a role in suppressing malignant alteration.

3. Effect of SNT-2 on ERK Activity

By the same way as mentioned previously, the above-described SNT-2 expression vector and Δ186-252 expression vector were prepared, and were transfected into Saos-2 cell which allows stable gene transfection. It should be noted that EGFR is endogenous in the Saos-2 cell. The Saos-2 cell expressing SNT-2 is herein after sometimes referred to as "SNT-2 transfectant". And, it was determined whether the phosphorylation of ERK and MEK which are intermediate molecules in the signaling pathway is down-regulated by exogenous SNT-2 after treatment of the cells with EGF. The EGF treatment was carried out after keeping the above-described cells in a serum deficiency state for 24 hours, under the condition of 50 ng/ml for 10 minutes. And, the cell lysate of every cell was analyzed by immunoblotting with various types of antibodies. Specifically, the phosphorylation of ERK and MEK were determined using anti-phosphorylated ERK antibody (anti-pERK antibody) and anti-phosphorylated MEK antibody (anti-pMEK antibody). And, the phosphorylation level of ERK and MEK was calculated using NIH image software.

Figure 4:
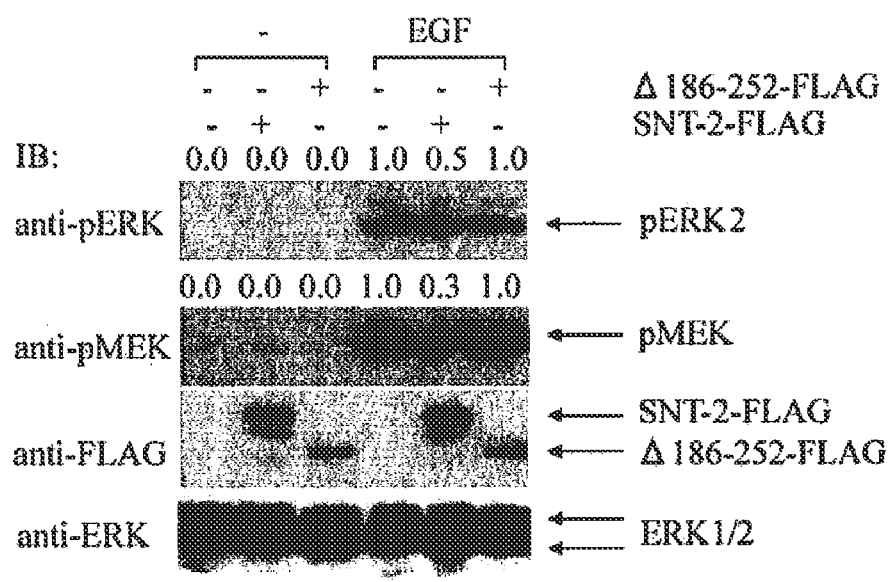
FIG. 4.
Figure 4:
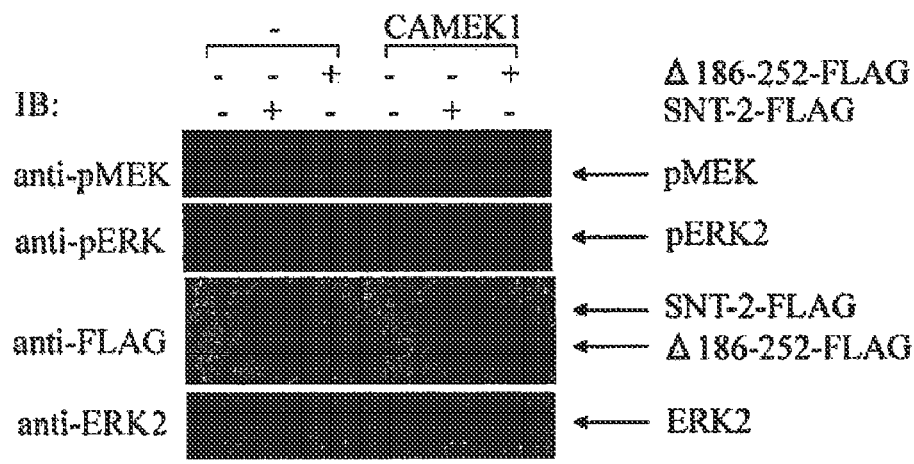

These results were shown in FIG. 4 (A). This figure shows photographs representing the results of immunoblotting of Saos-2 cells transfected with various types of expression vectors. In this figure, in columns of Δ186-252-FLAG and SNT-2-FLAG, "+" indicates the transfection of above-described SNT-2 expression vector and Δ186-252 expression vector, and "−" indicates the transfection of control vector having no insertion of objective gene in place of the above-described expression vectors. "−, EGF" indicate absence or presence of EGF stimulation. It should be noted that, these indications in the figure are herein after the same as above. As shown in the same figure, decrease of pERK and pMEK was observed in the cells which expressed SNT-2 when EGF stimulation was applied. From this result, it turned out that the phosphorylation of ERK and MEK could be down-regulated by the expression of SNT-2. Further, decrease of pERK and pMER was not observed in the cells which expressed Δ186-252. From this result, it was clarified that the 186th-the 252nd region in SNT-2 was the ERK2 binding domain. It should be noted that, as described herein later, by further analysis, it has been clarified that more narrow region of the 237th-the 252nd is the ERK2 binding domain.

The activated MEK (pMEK) is known to activate ERK, particularly by the phosphorylation of Thr-X-Thr motif. And so, confirmation on whether the phosphorylation of ERK2 by MEK is regulated directly or indirectly by SNT-2 was carried out. For the purpose of this confirmation, CAMEK1 expression vector which expresses constantly activated MEK1 variant (CAMEK1) was transfected into the above-described SNT-2 transfectant. And, by the same way as mentioned previously, phosphorylation of MEK and ERK2 was analyzed by immunoblotting.

These results were shown in FIG. 4 (B). This figure shows photographs representing the results of immunoblotting of Saos-2 cells which have been transfected with various types of expression vectors. As shown in the same figure, in the cells expressing constantly-active CAMEK1, phosphorylation of ERK2 by CAMEK1 was not suppressed by SNT-2 and Δ186-252 variant. This suggests that, even in the case where SNT-2 exists in large excess, activated pMEK1 phosphorylates ERK2. As described above, SNT-2 inhibits activation of ERK indirectly. It can be presumed from these results that SNT-2 down-regulates the phosphorylation of ERK2 through the reaction with EGF in the up-stream of MEK or in parallel with MEK. In addition, as an aspect, it can be presumed that binding of ERK2 with SNT-2 is important.

4. Effect of Interaction Between SNT-2 and ERK2 on the Signaling Through EGFR/Ras/ERK Pathway To determine the step where SNT-2 down-regulates the signaling from EGFR to MEK, in vitro binding assay for determining Ras activity was carried out.

Figure 5:
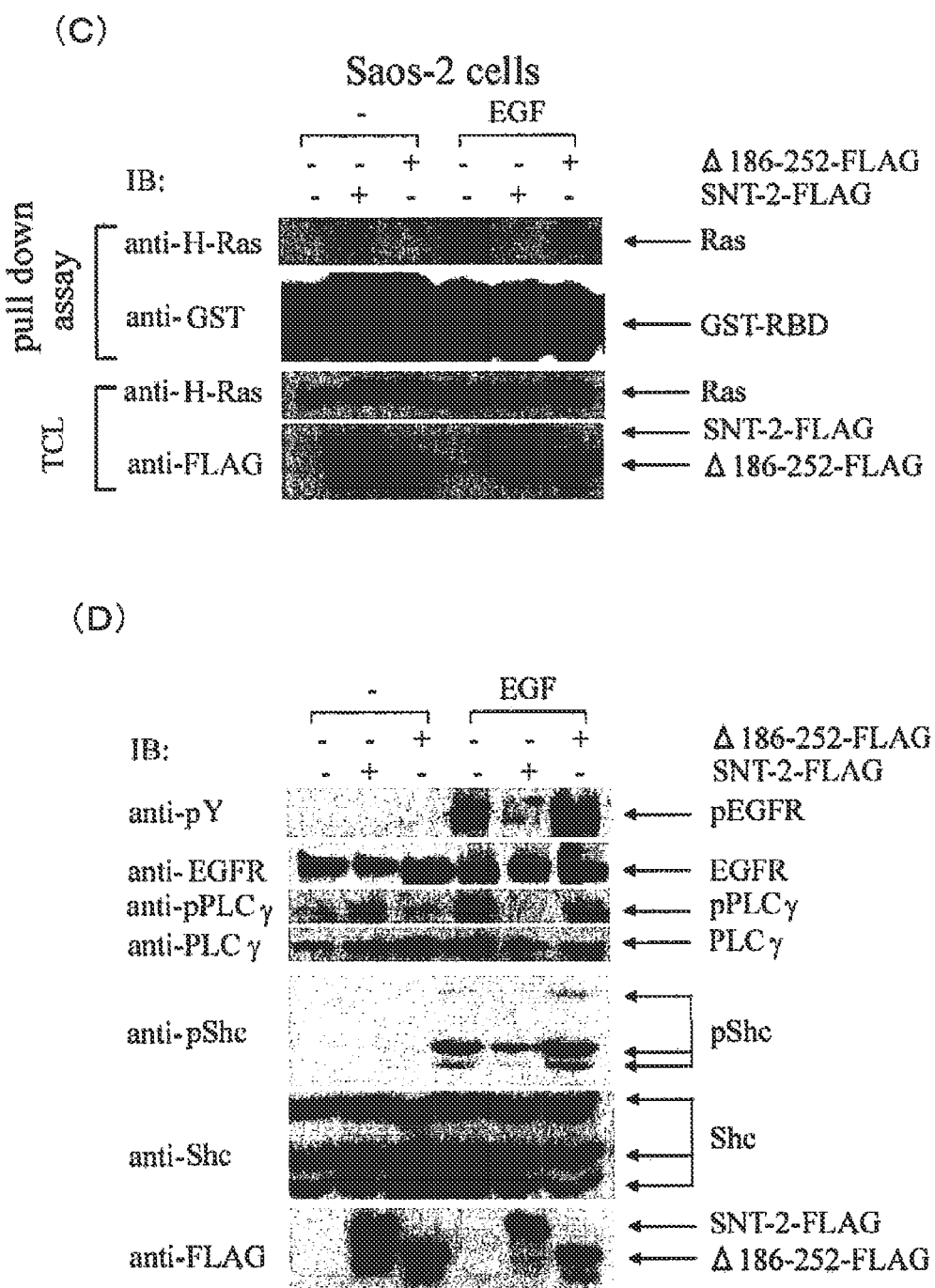
FIG. 5.

SNT-2 transfectant was treated with EGF, and the activated Ras level was measured by binding of Ras with Ras-binding domain (RBD) of Raf. These results were shown in FIG. 5 (C). FIG. 5 (C) shows photographs representing the results of immunoblotting of Saos-2 cells which have been transfected with various types of expression vectors. As shown in the same figure, the result was that the binding level of Ras to RBD was lower in the cells expressing SNT-2 than that in the cells transfected with control vector which is not inserted with the objective gene. However, in the cells expressing Δ186-252, the binding affinity was partially restored. This result suggests that the activation of R as or further upstream signaling is affected by SNT-2.

Shc and PLCg bind directly to autophosphorylated EGFR (autophosphorylated EGFR). For this reason, these proteins have been thought to be phosphorylated by activated EGFR (Literature 9). And so, determination of tyrosine phosphorylation level of Shc, PLCg and EGFR was carried out.
Literature 9: Yarden, Y. et al., Nat. Rev. Cell Biol. 2: 127-137 (2001)

The results were shown in FIG. 5 (D). FIG. 5 (D) shows photographs representing the results of immunoblotting of Saos-2 cells transfected with various types of expression vectors. As shown in the same figure, the phosphorylation level of these proteins was lower in the cells expressing SNT-2 than the cells expressing Δ186-252 and the cells transfected with control vector.

Figure 6:
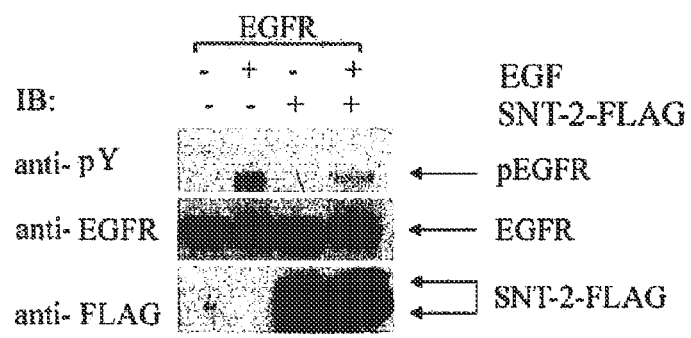
FIG. 6.

To confirm this result, EGFR expression vector and SNT-2 expression plasmid were transfected simultaneously into HEK293 cell, and the tyrosine phosphorylation of EGFR was determined. As the result, as shown in FIG. 6 (E), the tyrosine phosphorylation of EGFR was decreased by the expression of SNT-2. These results suggest that EGFR/R as/ERK signaling is down-regulated by SNT-2-ERK2 interaction in the step of autophosphorylation of EGFR.

5. Binding Affinity of SNT-2 for EGFR

Confirmation on whether SNT-2 binds with EGFR at the stage where the phosphorylation of EGFR is down-regulated by SNT-2 was carried out.

Figure 7:
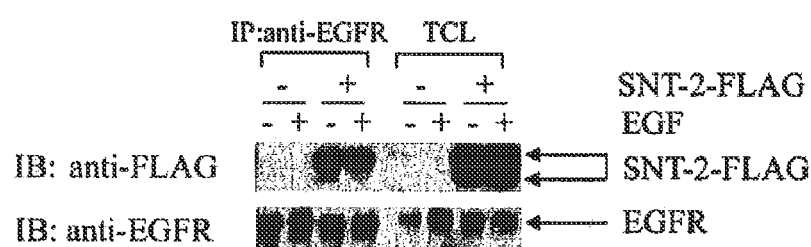
FIG. 7.
Figure 7:
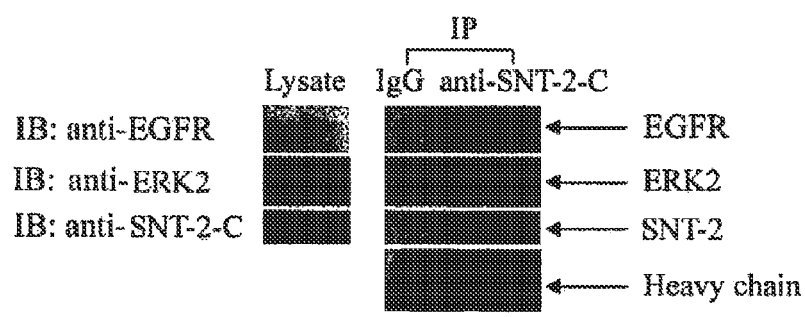

By means of immunoblotting with anti-FLAG antibody, immunocoprecipitation (IP) using anti-EGFR antibody was carried out for the cell lysate of SNT-2 transfectant. The results are shown in the upper column of FIG. 7 (A). The upper column of FIG. 7 (A) shows photographs representing the results of immunoblotting of Saos-2 cells which have been transfected with various types of expression vectors. As shown in the same figure, SNT-2 showed immunocoprecipitation with anti-EGFR antibody regardless of addition and non-addition of EGF.

In addition, to investigate interaction of foreign SNT-2, EGFR and ERK2, immunocoprecipitation of the cell lysate of mouse brain with anti-SNT-2-C antibody was carried out by immunoblotting with antibodies against EGFR, SNT-2 and ERK2. It should be noted that the antibody used here was biotinylated anti-SNT-2-C antibody. These results are shown in the lower column of FIG. 7 (A). The lower column of FIG. 7 (A) shows photographs representing the results of immunoblotting of Saos-2 cells which have been transfected with various types of expression vectors. As the result, it turned out that, in the cell lysate of mouse brain, SNT-2 interacted with EGFR and ERK2.

Figure 8:
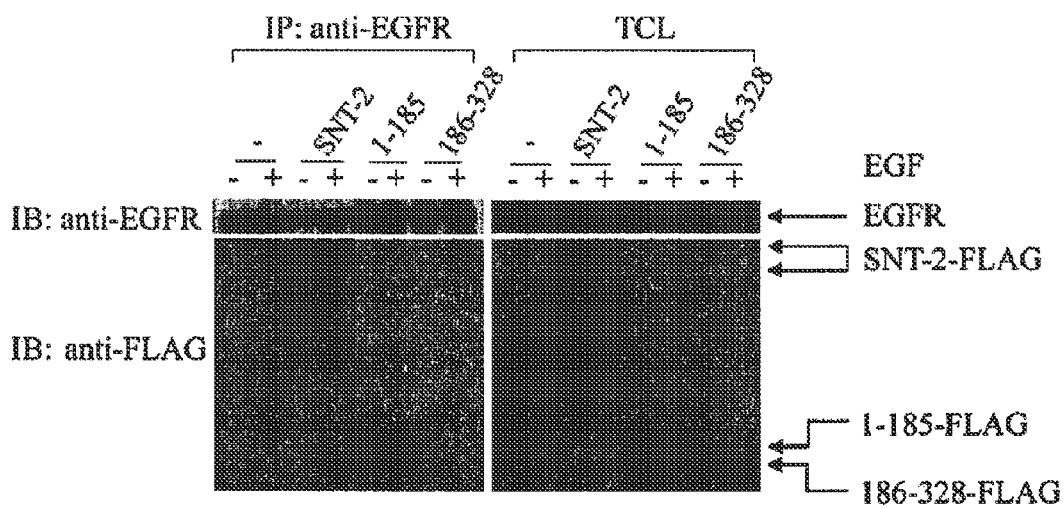
FIG. 8.
Figure 8:
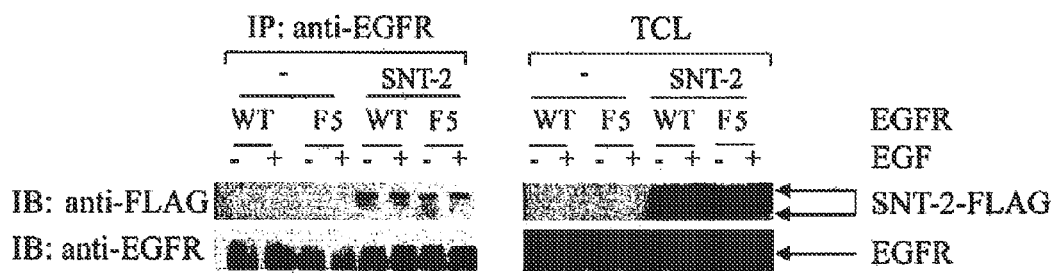

The region in SNT-2 which interacts with ERK2 was investigated. As an expression vector, SNT-2 expression vector which expresses the entire length of SNT-2, 1-185 expression vector which expresses PTB domain (the 1st-the 185th) of SNT-2 and 186-328 expression vector which expresses the 186th-the 328th region of SNT-2 were each transfected transiently into HEK293 cell. Schematic diagram of construction of these expression vectors were shown in FIG. 9 (A). And, for the cell lysate (TCL) of HEK293 cells which have been transfected with the expression vectors, immunocoprecipitation with anti-EGFR antibody was carried out. The results are shown in FIG. 8 (B). FIG. 8 (B) shows photographs representing the results of immunoblotting of transfected cells. As shown in the same figure, while the cells expressing the entire length of SNT-2 or 1-185 variant showed immunoprecipitation with anti-EGFR antibody, the cells expressing PTB-domain-deleted 186-328 variant did not show immunoprecipitation. From this result, it is suggested that EGFR binding domain is located in the PTB domain which is a mediator of FGF receptor and neurotrophin receptor.

In many cases, PTB domain binds with phosphorylated tyrosine residue, while, in the cells with serum deficiency state, SNT-2 binds with EGFR. And so, investigation on whether SNT-2 binds with phosphorylated tyrosine in the EGFR was carried out.

EGFR expression vector which expresses wild-type EGFR or F5 expression vector which expresses F5 variant of EGFR was transfected together with SNT-2 expression vector simultaneously into HEK293 cell. In the above-described F5, the main autophosphorylation site of EGFR was deleted. And, the cell lysate of this gene-transfected cell was subjected to immunocoprecipitation with anti-EGFR antibody. The results were shown in FIG. 8 (C). FIG. 8 (C) shows photographs representing the results of immunoblotting of the transfected cells. As shown in the same figure, SNT-2 showed interaction with F5 as well as with wild-type EGFR. For this reason, it turns out that SNT-2 binds with EGFR at the site other than the main site of tyrosine autophosphorylation of EGFR.

6. Effect of SNT-2 on the Activation of Other MAPKs

Figure 9:
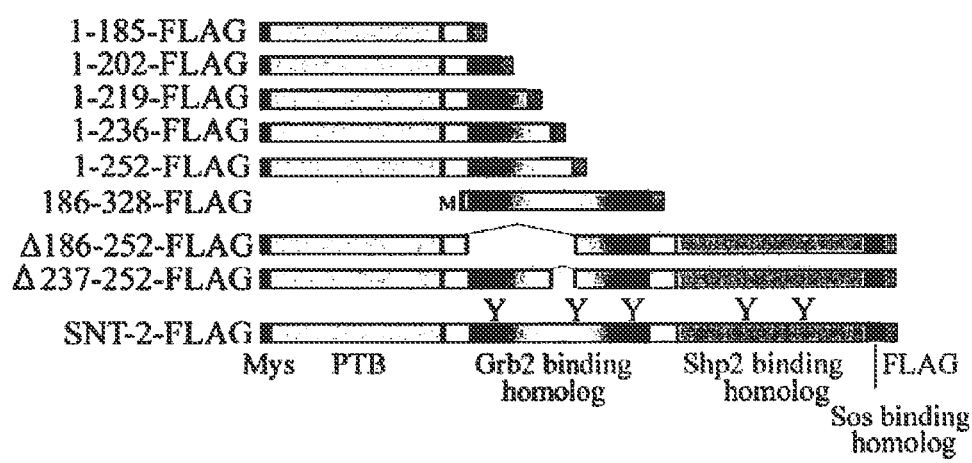
FIG. 9.

To narrow the region in SNT-2 which interacts with ERK2, various types of vectors which express FLAG tag-SNT-2 variants were prepared and expressed in HEK293 cell. For the above-described vector, as mentioned previously, 1-185 expression vector, 1-202 expression vector, 1-219 expression vector, 1-236 expression vector, 1-252 expression vector, 186-323 expression vector, Δ186-252 expression vector, Δ237-252 expression vector and SNT-2 expression vector were employed. In this respect, the schematic diagram of genes inserted in the expression vectors is shown in FIG. 9 (A).

Figure 10:
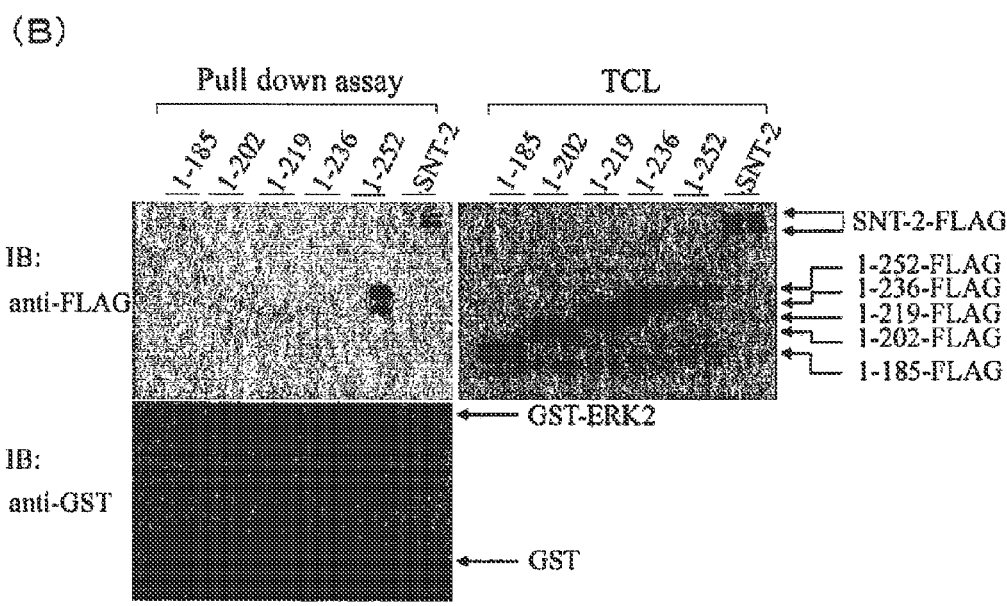
FIG. 10.
Figure 10:
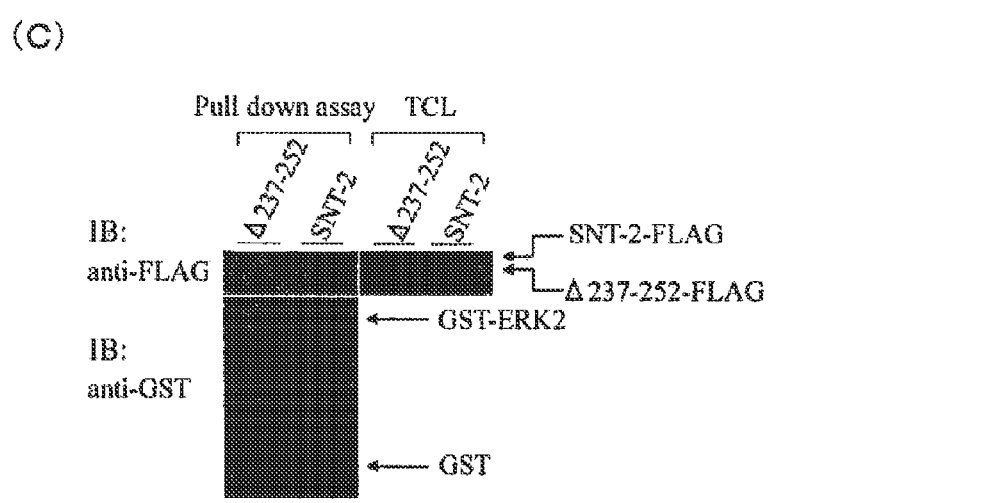

And, the solubilized preparation of the gene-transfected cells were subjected to pull down assay. The results are shown in FIGS. 10 (B) and (C). Both figures show photographs representing the results of immunoblotting of the transfected cells. As shown in the both figures, GST-ERK2 fusion protein bound with 1-252 variant, but did not bind with 1-236 variant and Δ237-252 variant. From these results, it turns out that the amino acid region of the 237th-the 252nd in SNT-2 is necessary for binding with ERK2.

Figure 11:
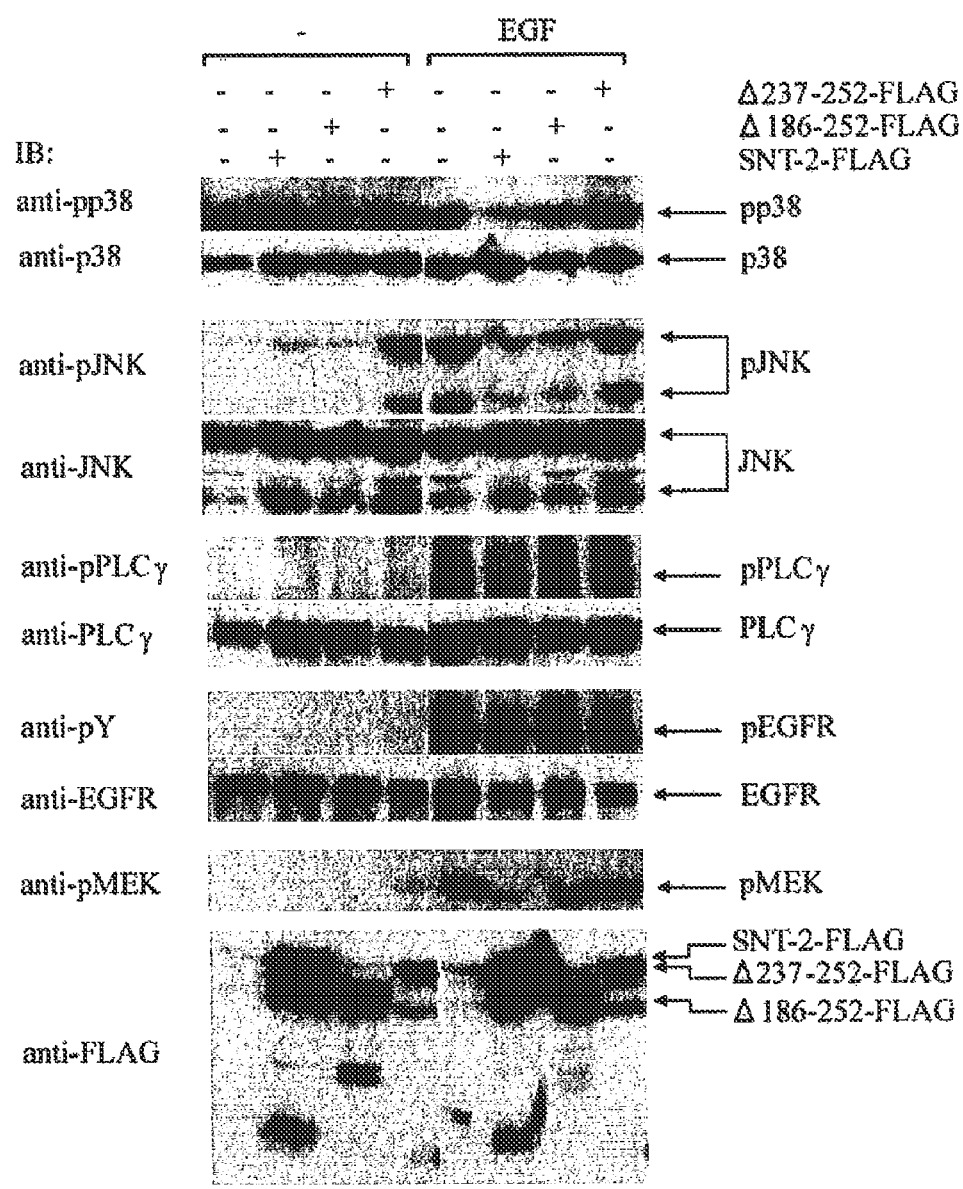
FIG. 11.

Further, to investigate the role of SNT-2 in EGF signaling, phosphorylation of JNK and p38 by EGF stimulation in Saos-2 cells expressing Δ237-252 variant with deletion of ERK2 binding domain and in Saos-2 cells expressing the entire length of SNT-2 were studied. Specifically, after the above-described cells transfected with various types of genes were kept serum deficiency state for 24 hours, the cells were treated with EGF (50 ng/ml) for 10 minutes. And, the lysate of the above-described cells was subjected to immunoblotting with the use of various types of antibodies. The results are shown in FIG. 11. This figure shows photographs representing the results of immunoblotting of the transfected cells. As shown in the same figure, the phosphorylation level of JNK and p38 was lower in the cells expressing SNT-2 than the cells transfected with control vector. In addition, the phosphorylation level of JNK and p38 in the cells expressing Δ237-252 variant was equivalent to that in the cells transfected with control vector. As mentioned above, from the fact that SNT-2 is capable of inhibiting the EGFR-mediated activation of various types of signal proteins, SNT-2 is speculated to be a target of SNT-2-ERK2 complex for down-regulation of EGFR signaling by EGFR.

7. Effect of Activation of ERK on EGFR Signaling

ERK2 binding domain (the 237th-the 252nd) of SNT-2 is presumed, as mentioned above, to be necessary for the inhibition effect by SNT-2 in EGF signaling. And so, confirmation on whether the activation of ERK is necessary for these effects was carried out.

Figure 12:
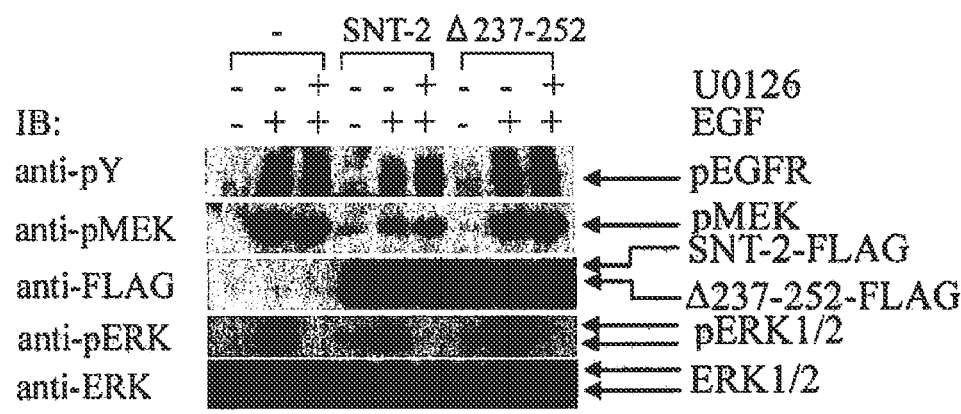
FIG. 12.

The cells transfected with SNT-2 expression vector, Δ237-252 variant expression vector, or control vector with no insertion of the objective gene were kept serum deficiency state for 24 hours, and after that, the cells were treated with MEK inhibitor of U0126 (10 μM) for 1.5 hours, and then treated with EGF (50 ng/ml). And, the cell lysate was subjected to immunoblotting with the use of various types of antibodies. The results are shown in FIG. 12. This figure shows photographs representing the results of immunoblotting of the gene-transfected cells. As shown in the same figure, it turned out that the phosphorylation level of EGFR and MEK was higher in the cells expressing SNT-2 with U0126 treatment as compared with the cells expressing SNT-2 without U0126 treatment. In contrast to this, the phosphorylation level of EGFR and NEK in the cells transfected with control vector was equivalent to that in the cells expressing Δ237-252 regardless of the treatment with U0126. From these results, it is speculated that activation of ERK plays an important role in the down-regulation of EGFR signal mediated by SNT-2-ERK2 complex.

8. Effect of SNT-2-ERK2 Complex on Cell Proliferation

The effect of SNT-2 on the cell proliferation was investigated. Here, to introduce the entire length of SNT-2 and Δ237-252 variant transiently into NIH 3T3 cell expressing EGFR, retrovirus system was used. It should be noted that, by the use of retrovirus system, transient expression of the transfected gene with about 100% of efficiency has been confirmed. And, the expression level of transcription product of foreign SNT-2 and SNT-1 in NIH 3T3 cell and mouse brain were measured. The results are shown in the upper column of FIG. 13 (A). The upper column of this figure shows photographs representing the results of northern blotting presenting the expression level of transcription products of SNT-2 and SNT-1. As shown in the same figure, the expression level of SNT-2 transcript in NIH 3T3 cell was much lower than that in the brain; on the other hand, the expression level of SNT-1 was high both in NIH 3T3 cell and in the brain. This suggested that the expression of SNT-1/Frs2α is eccentric; in contrast, SNT-2/Frs2β is expressed in high level in a restricted are a including, for example, nerve tissue. In addition, in the lower column of FIG. 13 (A), the results of western blotting analysis showing expression level of SNT-2 replication product and SNT-1 replication product are shown. As shown in this figure, the result that the expression level of SNT-2 in NIH 3T3 cell was similar to endogenous level in the brain was obtained.

Figure 13:
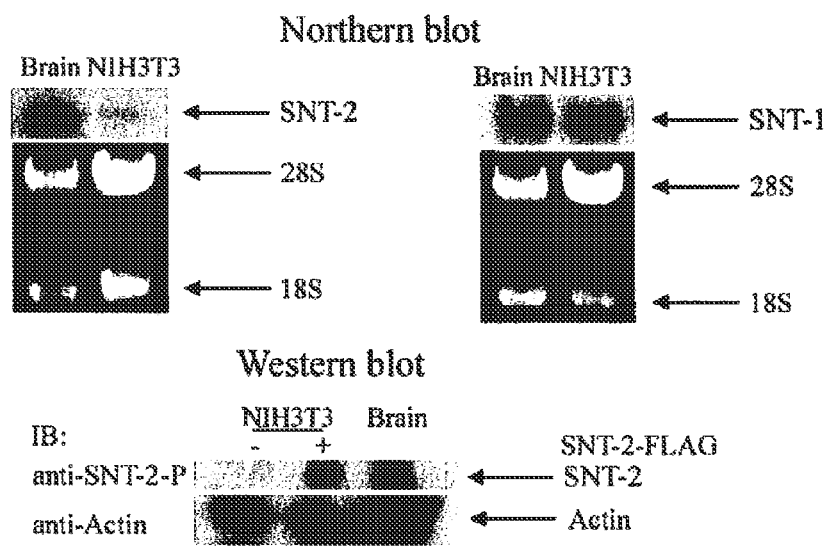
FIG. 13.
Figure 13:
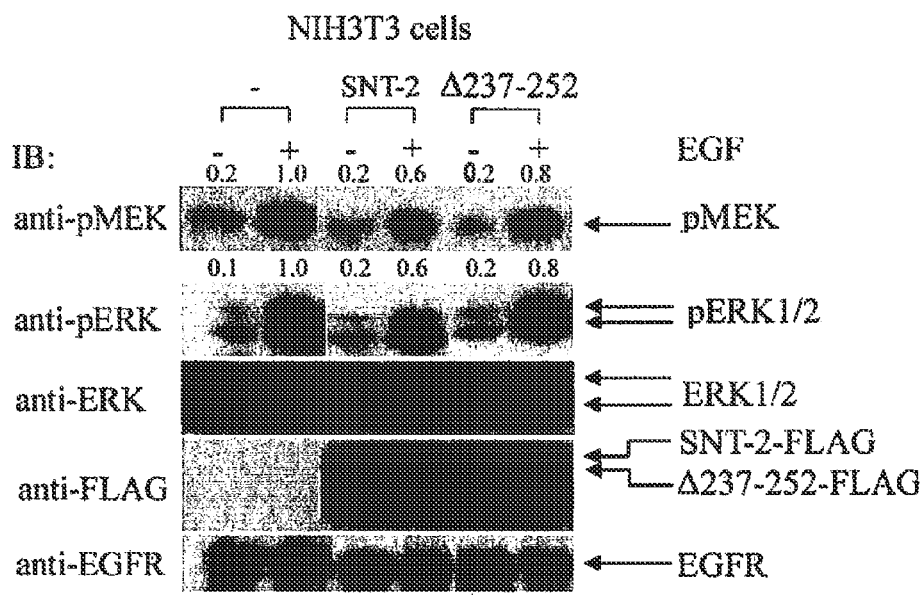

SNT-2 expression retrovirus vector, Δ237-252 expression retrovirus vector, or control vector without insertion of the objective gene was transfected into NIH 3T3 cell expressing EGFR. These transfectant cells were kept serum deficiency state for 24 hours, and after that, the cells were treated with EGF (50 ng/ml) for 10 minutes. And, the cell lysate was subjected to immunoblotting with the use of various types of antibodies. The phosphorylation level of MEK and ERK1/2 were calculated using NIH image software. The results are shown in FIG. 13 (B). This figure shows photographs representing the results of immunoblotting of NIH 3T3 cells transfected with retrovirus vector. As shown in the same figure, the phosphorylation level of MEK and ERK after EGF stimulation was lower in the cells expressing SNT-2 as compared with the cells transfected with control vector. In contrast to this, the phosphorylation level of MEK and ERK in the cells expressing Δ237-252 was restored to the same level as that in the cells transfected with control vector.

Figure 14:
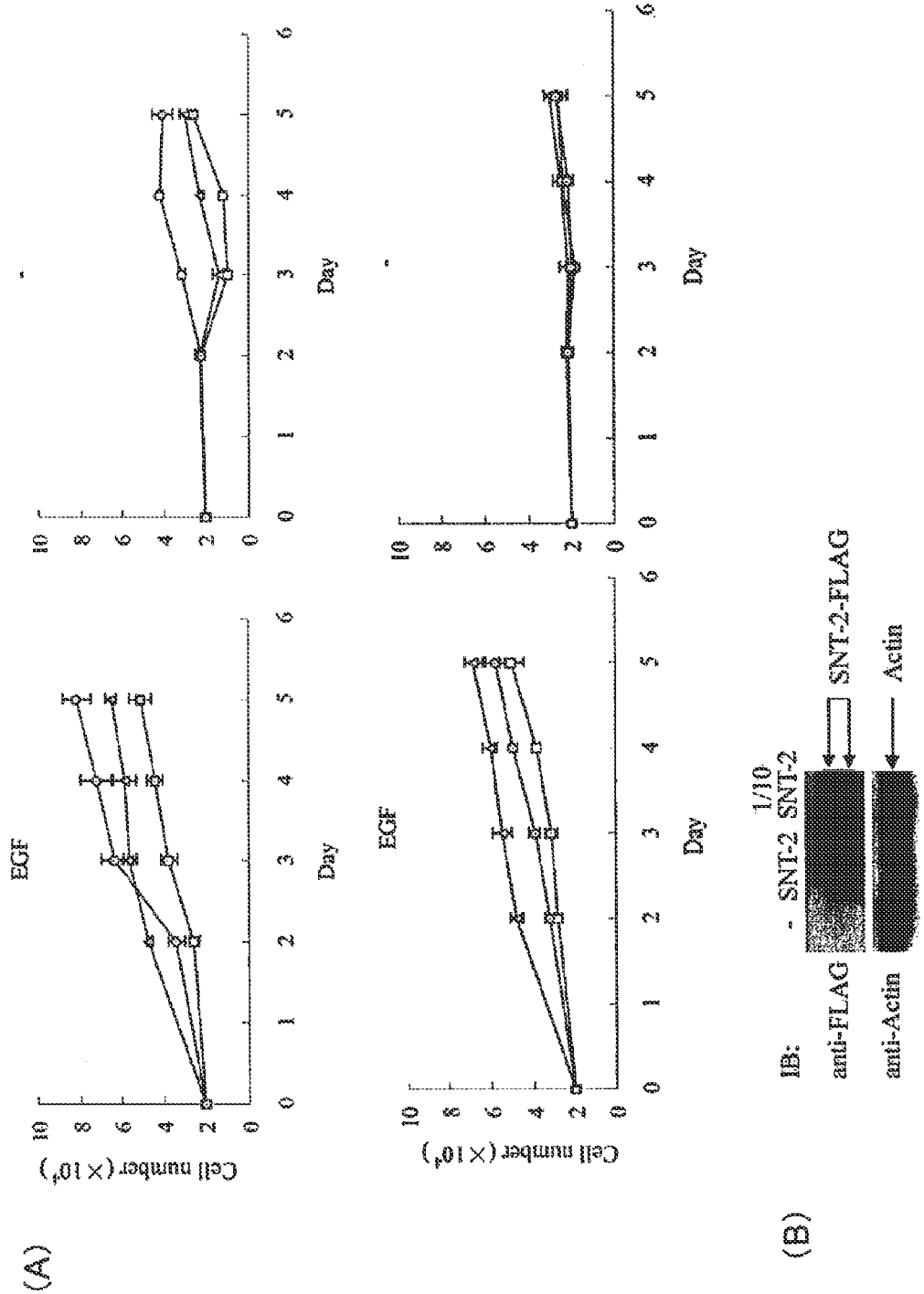
FIG. 14.

In addition, as to the above-described retrovirus-transfected NIH 3T3 cell, proliferation of the cell was assayed. The results are shown in FIG. 14 (A). This figure shows a graphical representation of change in the number of cells with time for the cells transfected with respective retrovirus vectors. In the same figure, Δ represents the results of the cells transfected with control vector; □ represents the cells expressing the entire length of SNT-2; represents the cells expressing Δ237-252. In addition, for the purpose of confirming inhibition effect by SNT-2, a diluted 1/10 concentration of SNT-2 expression retrovirus vector was transfected into NIH 3T3 cell, change in the number of cells was determined. The result of the non-dilution is represented by upper 2 graphs in the same figure; and the result of the 1/10 dilution is represented by lower 2 graphs in the same figure. As shown in FIG. 14 (A), under serum deficiency condition, significant increase of cell number was not observed in the transfected cells. And, by stimulation of cells with EGF (on day 3-5 of culture), effective proliferation was observed in the cells transfected with control vector. In addition, by stimulation of cells with EGF, proliferation of the cells expressing Δ237-252 was fast as compared with the cells transfected with control vector. Whereas, even after stimulation with EGF, proliferation of the cells expressing SNT-2 was slow as compared with other cells. In addition, when the transfection dosage of SNT-2 expression retrovirus vector was decreased to 1/10, fast proliferation was observed as compared with the cells received undiluted vector. It should be noted that, expression level of SNT-2 was determined by immunoblotting method using antibody. The results are shown in the lower figure of FIG. 14 (B). As shown in the same figure, when the transfection dosage of SNT-2 expression retrovirus vector was decreased to 1/10, the expression level of SNT-2 was decreased accordingly.

Figure 15:
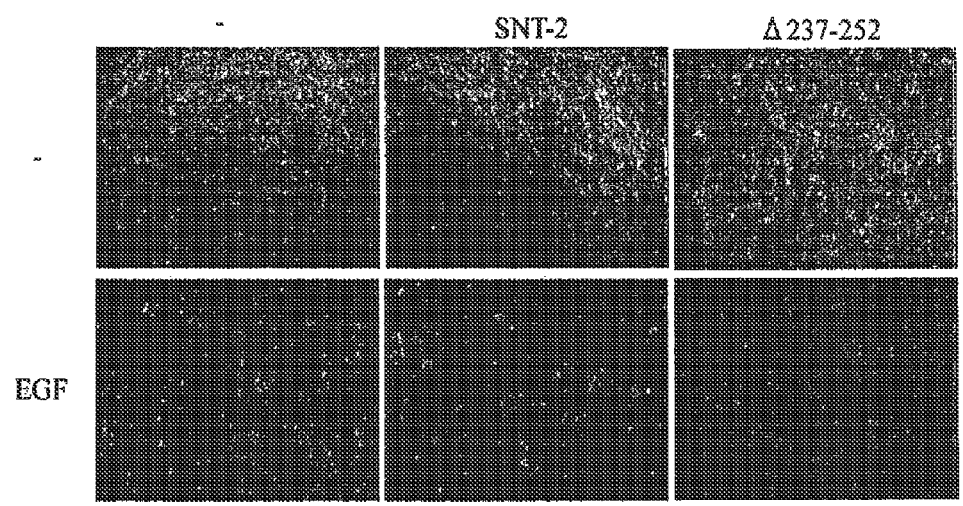
FIG. 15.
Figure 15:
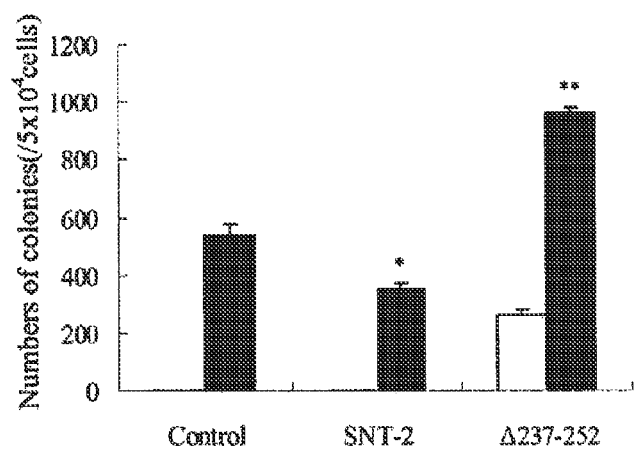

Next, investigation on whether the entire length of SNT-2 or Δ237-252 variant inhibits anchorage dependency of the cell independently of cell growth was carried out using soft agar colony assay. The results are shown in FIG. 15 (A). FIG. 15 (A) shows photographs representing colonies formed. In addition, FIG. 15 (B) shows the number of colonies of respective transfected cells; outline column indicates the result of no EGF treatment; black column indicates the result of EGF treatment. It should be noted that these results were come out from twice repeated data, and represented by mean±s.d. In addition, in the same figure, * indicates P<0.05, and ** indicates P<0.01. As shown in the same figure, when EGF treatment was not applied, colonies were confirmed in the cells expressing Δ237-252, where as in the NIH 3T3 cell transfected with control vector or in the cells transfected with SNT-2 expression vector did not form colony. In addition, when EGF treatment was applied, the cells expressing Δ237-252 showed more colonies than the cells transfected with control vector (increase by around 80%), where as in the cells expressing SNT-2, number of colonies was decreased significantly (decrease by around 35%). Further, in the presence of EGF, size of colonies of the cells expressing SNT-2 was smaller than that of the cells transfected with control vector or the cells expressing Δ237-252.

Example 2

Effect of FRS2β on the signaling of erbB2 was determined.
1. Effect of FRS2β on erbB2 and erbB3

It has been known that erbB2 forms heterodimer with erbB3 of the same erb family, and by this induction of dimerization, intracellular domain of the above-described receptor (erbB2 and erbB3) is activated. And so, the effect of FRS2β (SNT-2) on the activation of erbB2 and erbB3 was determined. In this regard, unless otherwise indicated, the determination was carried out by the same way as described in Example 1.

Coding sequences of cDNA of wild-type human erbB2 and human erbB3 were prepared based on NCBI database Accession No. NM_004448 (human erbB2) and Accession No. NM_001982 (human erbB3). And, this coding sequence was linked to a vector having CMV promoter by the same way as described in Example 1. The expression vector linked with the coding sequence of erbB2 is referred to as erbB2 expression vector, and the expression vector linked with the coding sequence of erbB3 is referred to as erbB3 expression vector. And, erbB2 expression vector, erbB3 expression vector and FRS2β expression vector (the above-described SNT-2 expression vector) was transfected transiently into HEK293T cell, respectively. And, the cells were cultured by the same way except for adding NRG (neuregulin) which is a ligand of erbB3 in place of EGF. And, the cell lysate of the cultured cells was subjected to the immunoblotting using the following antibodies. As for the antibody, anti-erbB2 antibody (OP15, Calbiochem) and anti-erbB3 antibody (C-17, Santa Cruz Biotechnology Inc.) were used.

Figure 16:
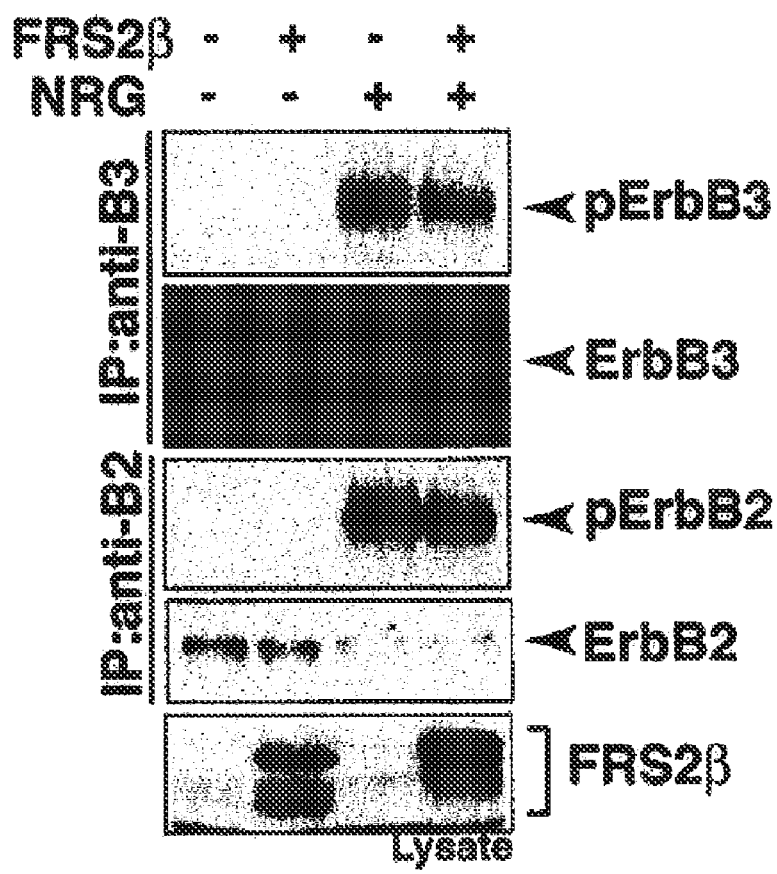
FIG. 16.

The results are shown in FIG. 16. This figure shows photographs representing the results of immunoblotting of the cells transfected with respective expression vectors. As shown in the same figure, phosphorylation of erbB3 and erbB2 in the cell introduced with FRS2β was suppressed as compared with the cell not introduced with FRS2β. From this result, it can be said that FRS2β inhibits the activation (phosphorylaton) of erbB2 and erbB3, and thereby, the signaling pathway of erbB2 is down-regulated.
2. Effect of FRS2β on Heterodimerization Confirmation of the effect of FRS2β on the formation of heterodimer composed of erbB2 and erbB3 in the signaling pathway was carried out.

Figure 17:
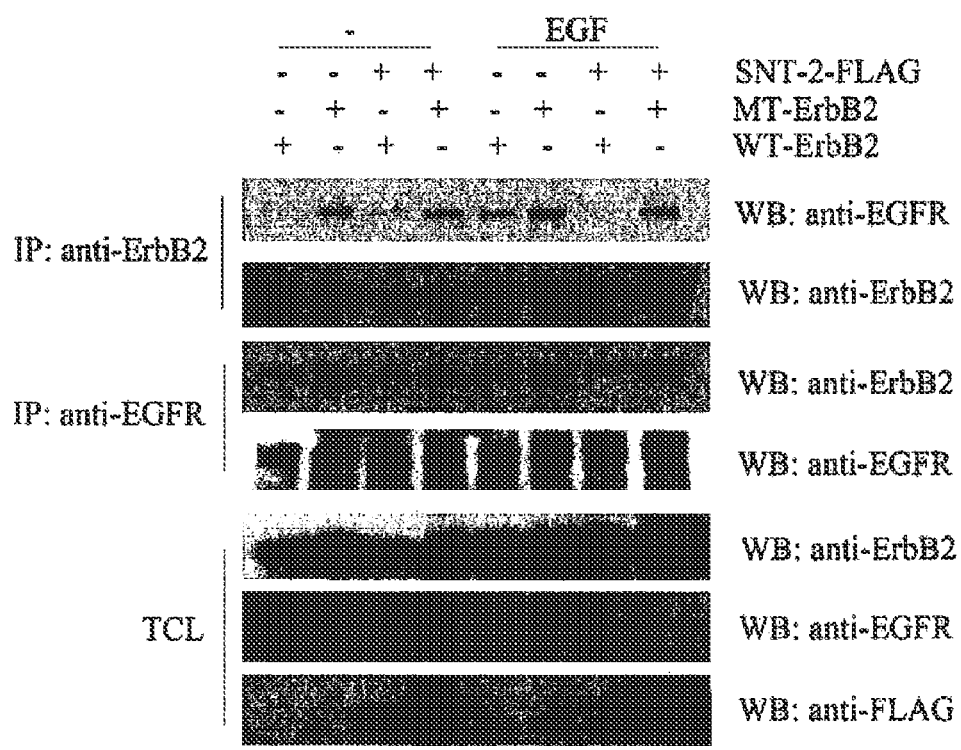
FIG. 17.

Each of EGFR expression vector, erbB2 expression vector and FRS2β expression vector was transfected transiently into HEK293T cell, and treated with EGF. The cell lysate of the transfected cells was immunoprecipitated with anti-EGFR antibody or anti-erbB2 antibody, and then subjected to immunoblotting using respective antibodies. The results are shown in FIG. 17. This figure shows photographs representing the results of the immunoblotting of the cells transfected with respective expression vectors.

As shown in the same figure, in the cell lysate of the cells which were not introduced with FRS2β, erbB2 was coprecipitated EGF-dependently with anti-EGFR antibody, and in addition, EGFR was coprecipitated with anti-erbB2 antibody.

On the other hand, in the cell lysate of the cells introduced with FRS2β, the amount of erbB2 or EGFR coprecipitated with EGFR or erbB2 was decreased. From the results described above, it can be said that FRS2β suppresses EGF-dependently the formation of EGFR-erbB2 heterodimer.

A coding sequence of erbB2 mutant which had been introduced with a mutation corresponding to that in a cell membrane-spanning domain present in rat breast cancer gene was prepared. And, this coding sequence was ligated to a vector having CMV promoter by the same way as described in Example 1. The expression vector ligated with the coding sequence of erbB2 mutant is referred to as erbB2 mutant expression vector. And, EGFR expression vector, erbB2 mutant expression vector and FRS2β expression vector was each transfected transiently into HER293T cell, and treated with EGF. The cell lysate of the transfected cells was immunoprecipitated with anti-EGFR antibody or anti-erbB2 antibody, and then subjected to immunoblotting using respective antibody. In the cell lysate of the cells which were not introduced with FRS2β, erbB2 mutant was immunocoprecipitated EGF-dependently with anti-EGFR antibody, and in addition, EGFR was immunocoprecipitated with anti-erbB2 antibody. On the other hand, in the cell lysate of the cells introduced with FRS2β, the amount of EGFR or erbB2 mutant in the immunocoprecipitated EGFR or erbB2 mutant was decreased. From the results described above, it can be said that FRS2β suppresses EGF-dependently the formation of EGFR-erbB2 mutant heterodimer.

3. Tendency of erbB2 and FRS2β in Patient with Breast Cancer

Confirmation of expression of FRS2β (SNT-2) in cancer tissue of a patient with breast cancer was carried out, and comparisons of the expression of FRS2β with the expression of erbB2/HER2/neu in the same patient were carried out.

The breast cancer tissues having the following 5 histological types were collected from patient. For these tissues, Hercep test was carried out according to the protocol, and determined by 4 stages. On the other hand, for the same breast cancer tissue, determination of erbB2 expression was carried out by immunostaining using anti-erbB2 antibody. Specifically, first, the respective breast cancer tissue was formalin-fixed, and deparafinized, and then the tissues were treated with 10 mM citrate buffer (pH 6) for 20 minutes by autoclaving. After that, the post-treatment breast cancer tissues were incubated with 100 times dilution of the above-described anti-FRS2β antibody at room temperature for 1 hour. The post-incubation breast cancer tissues were then stained by immunostaining using LASBC kit (product name, produced by Dako Japan) according to the attached protocol. As a coloring agent, 3,3'-diaminobenzidine was used. In addition, nuclear staining was performed using hematoxyline. The results are shown in the following table.

TABLE 1

| Tissue type | erbB2 HER2/neu | FRS2β SNT-2 |
|---|---|---|
| Sample 1 scirrhous carcinoma | 3+ | negative |
| Sample 2 papillotubular carcinoma | 2+ | negative |
| Sample 3 solid tubular carcinoma | 1+ | negative |
| Sample 4 invasive lobular carcinoma | 0 | positive |
| Sample 5 scirrhous carcinoma | 0 | positive |
| Sample 6 scirrhous carcinoma | 0 | positive |

As described above, the samples judged as erbB2 overexpression by Hercep test (Sample 1-3) was FRS2β (−), and the sample judged as no erbB2 overexpression (Sample 4-5) was FRS2β (+). From this result, it can be considered that the expression of FRS2β and the expression of erbB2/HER2/neu are in opposite correlation. In addition, it can be considered that the expression of FRS2β is possible to play a role in amplification of erbB2/HER2/neu by some sort of mechanism.

INDUSTRIAL APPLICABILITY

As described above, according to the polypeptide of the present invention, the above-described signaling pathway may be down-regulated. Therefore, for example, by introducing the polypeptide of the present invention or the nucleic acid capable of expressing the polypeptide of the present invention into human target cell, the above signaling in the above-described cell can be suppressed. Further, from the fact that the signaling of erbB1 or erbB2 is involved in the development of cancer as described above, prevention of the development of cancer and also treatment of the cancer may be performed by way of inhibiting signaling according to the present invention. In addition, also from the fact that, by the above-described inhibition of signaling, malignant alteration of cell as well as proliferation of cell can be suppressed, it can be said that the present invention is useful for the treatment of cancer.

In addition, because of the fact that the signaling of erbB1 or erbB2 is down-regulated by FRS2β, by detecting FRS2β in the target cell, determination on whether the above-described signaling is working can also be performed. And, on the basis of the result of the determination, for example, judgment on the necessity of treatment with anti-erbB1 antibody or anti-erbB2 antibody which inhibits the function of erbB1 or erbB2 can be made. As stated above, it can be said that the present invention is a quite useful technology, for example, in the field of medicine and molecular cytology.

What is claimed is:

1. A method for determining presence of down-regulation of a signaling pathway, wherein:
   said signaling pathway is mediated by erbB1 in a human cell; and
   said method comprises
   detecting one or both of human FRS2β protein and a transcript of human FRS2β gene in a human cell; and
   determining that down-regulation of a signaling pathway mediated by erbB1 is present in the human cell when the detected amount of said human FRS2β protein and/or said transcript of human FRS2β gene is significantly decreased compared to that detected in a normal human cell.

2. A method for determining necessity of treatment of a human cancer cell with an anticancer drug, wherein:
   said anticancer drug comprises an anti-human erbB1 antibody, and
   said method comprises
   detecting one or both of human FRS2β protein and a transcript of human FRS2β gene in a human cancer cell; and
   determining that treatment with an anticancer drug comprising an anti-human erbB1 antibody is necessary when the detected amount of said human FRS2β protein and/or said transcript of human FRS2β gene is significantly decreased compared to that detected in a normal human cell.

* * * * *

SEQUENCE LISTING

```
<160> NUMBER OF SEQ ID NOS: 6

<210> SEQ ID NO 1
<211> LENGTH: 492
<212> TYPE: PRT
<213> ORGANISM: Homo sapiens

<400> SEQUENCE: 1

Met Gly Ser Cys Cys Ser Cys Leu Asn Arg Asp Ser Val Pro Asp Asn
1               5                   10                  15

His Pro Thr Lys Phe Lys Val Thr Asn Val Asp Asp Glu Gly Val Glu
```

```
                    20                  25                  30
Leu Gly Ser Gly Val Met Glu Leu Thr Gln Ser Glu Leu Val Leu His
                35                  40                  45

Leu His Arg Arg Glu Ala Val Arg Trp Pro Tyr Leu Cys Leu Arg Arg
    50                  55                  60

Tyr Gly Tyr Asp Ser Asn Leu Phe Ser Phe Glu Ser Gly Arg Arg Cys
65                  70                  75                  80

Gln Thr Gly Gln Gly Ile Phe Ala Phe Lys Cys Ser Arg Ala Glu Glu
                85                  90                  95

Ile Phe Asn Leu Leu Gln Asp Leu Met Gln Cys Asn Ser Ile Asn Val
        100                 105                 110

Met Glu Glu Pro Val Ile Ile Thr Arg Asn Ser His Pro Ala Glu Leu
            115                 120                 125

Asp Leu Pro Arg Ala Pro Gln Pro Pro Asn Ala Leu Gly Tyr Thr Val
        130                 135                 140

Ser Ser Phe Ser Asn Gly Cys Pro Gly Glu Gly Pro Arg Phe Ser Ala
145                 150                 155                 160

Pro Arg Arg Leu Ser Thr Ser Ser Leu Arg His Pro Ser Leu Gly Glu
                165                 170                 175

Glu Ser Thr His Ala Leu Ile Ala Pro Asp Glu Gln Ser His Thr Tyr
            180                 185                 190

Val Asn Thr Pro Ala Ser Glu Asp His Arg Gly Arg His Cys
        195                 200                 205

Leu Gln Pro Leu Pro Glu Gly Gln Ala Pro Phe Leu Pro Gln Ala Arg
        210                 215                 220

Gly Pro Asp Gln Arg Asp Pro Gln Val Phe Leu Gln Pro Gly Gln Val
225                 230                 235                 240

Lys Phe Val Leu Gly Pro Thr Pro Ala Arg Arg His Met Val Lys Cys
                245                 250                 255

Gln Gly Leu Cys Pro Ser Leu His Asp Pro Pro His His Asn Asn Asn
            260                 265                 270

Asn Glu Ala Pro Ser Glu Cys Pro Ala Gln Pro Lys Cys Thr Tyr Glu
        275                 280                 285

Asn Val Thr Gly Gly Leu Trp Arg Gly Ala Gly Trp Arg Leu Ser Pro
        290                 295                 300

Glu Glu Pro Gly Trp Asn Gly Leu Ala His Arg Ala Ala Leu Leu
305                 310                 315                 320

His Tyr Glu Asn Leu Pro Pro Leu Pro Pro Val Trp Glu Ser Gln Ala
                325                 330                 335

Gln Gln Leu Gly Gly Glu Ala Gly Asp Asp Gly Asp Ser Arg Asp Gly
            340                 345                 350

Leu Thr Pro Ser Ser Asn Gly Phe Pro Asp Gly Glu Glu Asp Glu Thr
        355                 360                 365

Pro Leu Gln Lys Pro Thr Ser Thr Arg Ala Ala Ile Arg Ser His Gly
        370                 375                 380

Ser Phe Pro Val Pro Leu Thr Arg Arg Gly Ser Pro Arg Val Phe
385                 390                 395                 400

Asn Phe Asp Phe Arg Arg Pro Gly Pro Glu Pro Arg Gln Leu Asn
        405                 410                 415

Tyr Ile Gln Val Glu Leu Lys Gly Trp Gly Gly Asp Arg Pro Lys Gly
                420                 425                 430

Pro Gln Asn Pro Ser Ser Pro Gln Ala Pro Met Pro Thr Thr His Pro
            435                 440                 445
```

Ala Arg Ser Ser Asp Ser Tyr Ala Val Ile Asp Leu Lys Lys Thr Val
450                 455                 460

Ala Met Ser Asn Leu Gln Arg Ala Leu Pro Arg Asp Asp Gly Thr Ala
465                 470                 475                 480

Arg Lys Thr Arg His Asn Ser Thr Asp Leu Pro Leu
                485                 490

<210> SEQ ID NO 2
<211> LENGTH: 1479
<212> TYPE: DNA
<213> ORGANISM: Homo sapiens

<400> SEQUENCE: 2

```
atgggagct gctgcagctg cctgaacaga gacagcgttc cagacaacca ccccaccaag      60
ttcaaggtga caaatgtgga tgatgagggg gtggagctgg gctctggggt gatggagctg     120
acgcagagtg agctggtgct gcacctgcat cggcgtgagg ccgtccgctg gccttatctc     180
tgcttgcggc gctatggcta cgactccaac ctcttctcct ttgagagtgg ccgccgatgt     240
cagacaggcc agggaatatt tgcatttaag tgttcccggg ctgaggaaat cttcaacctc     300
cttcaggatc tgatgcagtg caacagcatc aatgtgatgg aagagcctgt catcatcacc     360
cgcaatagcc accccgctga gcttgacctc cctcgagccc ccagccacc caatgctcta      420
ggctacactg tctccagctt tccaatggc tgccctggag agggcccacg attctcagct      480
ccccggcggc tctcgacaag cagcctgcgg caccccctcgc ttggggaaga gtccacccat    540
gccctcattg ctcctgatga gcagtcccac acctatgtca acacaccggc cagtgaagat    600
gaccaccgca ggggccgcca ctgcctgcag cccctgcctg agggtcaggc accttcctc     660
ccgcaggccc gggaccctga ccaacgggac ccacaggtgt tcttgcagcc aggccaggtg    720
aagtttgtgt tgggcccgac ccctgctcgg cggcacatgg tgaagtgcca gggcctctgt   780
cccagcctgc atgaccccc acaccacaat aataacaatg aggccccttc tgagtgtcca    840
gcccagccca agtgcaccta cgagaacgtc accgggggc tgtggcgagg ggctggctgg    900
agactgagcc agaggagcc gggctggaat ggccttgccc accgccggc cgccctgctg      960
cactatgaga acctgccccc actgcccct gtgtgggaaa gccaagccca gcagctggga   1020
ggggaggctg gggatgatgg ggactcgagg gatgggctca cccctcttc caatggcttc   1080
cctgatggtg aggaggacga ccccactg cagaagccca ccagcaccg ggccgccatc    1140
cgcagccacg gcagctttcc tgtgccactg accgccgcc gcggctcccc aagggtcttc   1200
aactttgatt tccgccggcc ggggcccgag cccccaaggc agcttaacta catccaggtg    1260
gagctaaagg gctggggtgg agaccgcct aaggggcccc agaaccctc gagccccaa       1320
gcccccatgc ccaccacca ccctgcccga agctcagact cctacgccgt gattgacctc    1380
aaaaagaccg tggccatgtc caacctgcag agagctctgc ccgagacga tggcaccgcc    1440
aggaaaaccc ggcacaacag caccgacctg cctctgtag                           1479
```

<210> SEQ ID NO 3
<211> LENGTH: 185
<212> TYPE: PRT
<213> ORGANISM: Homo sapiens

<400> SEQUENCE: 3

Met Gly Ser Cys Cys Ser Cys Leu Asn Arg Asp Ser Val Pro Asp Asn
1               5                   10                  15

His Pro Thr Lys Phe Lys Val Thr Asn Val Asp Asp Glu Gly Val Glu
                20                  25                  30

Leu Gly Ser Gly Val Met Glu Leu Thr Gln Ser Glu Leu Val Leu His
            35                  40                  45

Leu His Arg Arg Glu Ala Val Arg Trp Pro Tyr Leu Cys Leu Arg Arg
 50                  55                  60

Tyr Gly Tyr Asp Ser Asn Leu Phe Ser Phe Glu Gly Arg Arg Cys
 65                  70                  75                  80

Gln Thr Gly Gln Gly Ile Phe Ala Phe Lys Cys Ser Arg Ala Glu Glu
                 85                  90                  95

Ile Phe Asn Leu Leu Gln Asp Leu Met Gln Cys Asn Ser Ile Asn Val
                100                 105                 110

Met Glu Glu Pro Val Ile Ile Thr Arg Asn Ser His Pro Ala Glu Leu
            115                 120                 125

Asp Leu Pro Arg Ala Pro Gln Pro Pro Asn Ala Leu Gly Tyr Thr Val
        130                 135                 140

Ser Ser Phe Ser Asn Gly Cys Pro Gly Glu Gly Pro Arg Phe Ser Ala
145                 150                 155                 160

Pro Arg Arg Leu Ser Thr Ser Ser Leu Arg His Pro Ser Leu Gly Glu
                165                 170                 175

Glu Ser Thr His Ala Leu Ile Ala Pro
            180                 185

<210> SEQ ID NO 4
<211> LENGTH: 555
<212> TYPE: DNA
<213> ORGANISM: Homo sapiens

<400> SEQUENCE: 4
atggggagct gctgcagctg cctgaacaga gacagcgttc cagacaacca ccccaccaag      60
ttcaaggtga caaatgtgga tgatgagggg gtggagctgg gctctggggt gatggagctg     120
acgcagagtg agctggtgct gcacctgcat cggcgtgagg ccgtccgctg gccttatctc     180
tgcttgcggc gctatggcta cgactccaac ctcttctcct ttgagagtgg ccgccgatgt     240
cagacaggcc agggaatatt tgcatttaag tgttcccggg ctgaggaaat cttcaacctc     300
cttcaggatc tgatgcagtg caacagcatc aatgtgatgg aagagcctgt catcatcacc     360
cgcaatagcc accccgctga gcttgacctc cctcgagccc cccagccacc caatgctcta     420
ggctacactg tctccagctt ttccaatggc tgccctggag agggcccacg attctcagct     480
ccccggcggc tctcgacaag cagcctgcgg caccccctcgc ttggggaaga gtccacccat     540
gccctcattg ctcct                                                       555

<210> SEQ ID NO 5
<211> LENGTH: 16
<212> TYPE: PRT
<213> ORGANISM: Homo sapiens

<400> SEQUENCE: 5

Pro Gly Gln Val Lys Phe Val Leu Gly Pro Thr Pro Ala Arg Arg His
1               5                   10                  15

<210> SEQ ID NO 6
<211> LENGTH: 48
<212> TYPE: DNA
<213> ORGANISM: Homo sapiens

<400> SEQUENCE: 6
ccaggccagg tgaagtttgt gttgggcccg acccctgctc ggcggcac        48